(12) United States Patent
Liu et al.

(10) Patent No.: US 11,935,159 B2
(45) Date of Patent: *Mar. 19, 2024

(54) METHOD AND SYSTEM FOR CALIBRATING AN IMAGING SYSTEM

(71) Applicant: SHANGHAI UNITED IMAGING HEALTHCARE CO., LTD., Shanghai (CN)

(72) Inventors: Weiping Liu, Shanghai (CN); Xiaoyue Gu, Shanghai (CN); Youjun Sun, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/161,870

(22) Filed: Jan. 30, 2023

(65) Prior Publication Data

US 2023/0169703 A1    Jun. 1, 2023

Related U.S. Application Data

(63) Continuation of application No. 17/156,708, filed on Jan. 25, 2021, now Pat. No. 11,568,583, which is a
(Continued)

(30) Foreign Application Priority Data

| Sep. 30, 2016 | (CN) | 201621099638.6 |
| Nov. 21, 2016 | (CN) | 201611039000.8 |
| May 4, 2017 | (CN) | 201710308861.X |

(51) Int. Cl.
G06T 11/00    (2006.01)
A61B 6/00    (2006.01)
(Continued)

(52) U.S. Cl.
CPC ............ *G06T 11/005* (2013.01); *A61B 6/037* (2013.01); *A61B 6/107* (2013.01); *A61B 6/4275* (2013.01);
(Continued)

(58) Field of Classification Search
CPC ............... G06T 11/005; G06T 2210/41; G01T 2210/41; A61B 6/037; A61B 6/583
See application file for complete search history.

(56) References Cited

U.S. PATENT DOCUMENTS

| 10,902,646 B2 | 1/2021 | Liu et al. | |
| 11,568,583 B2 * | 1/2023 | Liu et al. | A61B 6/4275 |

(Continued)

FOREIGN PATENT DOCUMENTS

| CN | 101036596 A | 9/2007 |
| CN | 102641200 A | 8/2012 |

(Continued)

OTHER PUBLICATIONS

International Search Report in PCT/CN2017/104779 dated Dec. 29, 2017, 5 pages.
(Continued)

*Primary Examiner* — Andrew W Johns
(74) *Attorney, Agent, or Firm* — METIS IP LLC

(57) ABSTRACT

The disclosure relates to a system and method for medical imaging. The method may include: move, by a motion controller, a phantom along an axis of a scanner to a plurality of phantom positions; acquire, by a scanner of the imaging device, a first set of PET data relating to the phantom at the plurality of phantom positions; and store the first set of PET data as an electrical file. The length of an axis of the phantom may be shorter than the length of an axis of the scanner, and at least one of the plurality of phantom positions may be inside a bore of the scanner.

20 Claims, 20 Drawing Sheets

Related U.S. Application Data continuation of application No. 16/237,145, filed on Dec. 31, 2018, now Pat. No. 10,902,646, which is a continuation of application No. PCT/CN2017/104779, filed on Sep. 30, 2017.

(51) Int. Cl.

| | | |
|---|---|---|
| *A61B 6/03* | (2006.01) | |
| *A61B 6/10* | (2006.01) | |
| *G01T 1/29* | (2006.01) | |
| *G01T 7/00* | (2006.01) | |
| *A61B 6/04* | (2006.01) | |

(52) U.S. Cl.
CPC .......... *A61B 6/4429* (2013.01); *A61B 6/4452* (2013.01); *A61B 6/4476* (2013.01); *A61B 6/5205* (2013.01); *A61B 6/5258* (2013.01); *A61B 6/583* (2013.01); *A61B 6/587* (2013.01); *G01T 1/2985* (2013.01); *G01T 7/005* (2013.01); *G06T 11/008* (2013.01); *A61B 6/0407* (2013.01); *A61B 6/0487* (2020.08); *G06T 2210/41* (2013.01)

(56) References Cited

U.S. PATENT DOCUMENTS

| | | | |
|---|---|---|---|
| 2003/0178559 | A1 | 9/2003 | Hamill et al. |
| 2004/0195512 | A1 | 10/2004 | Crosetto |
| 2004/0206897 | A1 | 10/2004 | Conti et al. |
| 2007/0172020 | A1 | 7/2007 | Nambu |
| 2007/0176087 | A1 | 8/2007 | Wang et al. |
| 2014/0119611 | A1 | 5/2014 | Prevrhal et al. |
| 2015/0260857 | A1 | 9/2015 | Zhang et al. |
| 2015/0276949 | A1 | 10/2015 | Grobshtein et al. |

FOREIGN PATENT DOCUMENTS

| | | |
|---|---|---|
| CN | 202537939 U | 11/2012 |
| CN | 102949192 A | 3/2013 |
| CN | 103006252 A | 4/2013 |
| CN | 103720571 A | 4/2014 |
| CN | 104799879 A | 7/2015 |
| CN | 104825185 A | 8/2015 |
| CN | 204654970 U | 9/2015 |
| CN | 105193441 A | 12/2015 |
| CN | 105411618 A | 3/2016 |
| CN | 105913397 A | 8/2016 |
| CN | 105976413 A | 9/2016 |
| CN | 106344059 A | 1/2017 |
| CN | 106618618 A | 5/2017 |
| CN | 107049352 A | 8/2017 |
| CN | 206526057 U | 9/2017 |
| JP | 2012055393 A | 3/2012 |

OTHER PUBLICATIONS

Written Opinion in PCT/CN2017/104779 dated Dec. 29, 2017, 5 pages.
First Office Action in Chinese Application No. 201611039000.8 dated Mar. 21, 2019, 16 pages.
The Second Office Action in Chinese Application No. 201611039000.8 dated Oct. 9, 2019, 16 pages.
First Office Action in Chinese Application No. 201710308861.X dated Oct. 8, 2019, 28 pages.
The Second Office Action in Chinese Application No. 201710308861.X dated Jun. 3, 2020, 26 pages.
Extended European Search Report in European Application No. 17855027.3 dated Jul. 12, 2019, 8 pages.
Falk Ponisch et al., Attenuation Correction of Four Dimensional (4D) PET Using Phase-correlated 4D-computed Tomography, Physics Medicine Biology, 53: 259-268, 2008.

* cited by examiner

1000

```
┌─────────────────────────────────────────────────────────┐
│ Extracting a second set of PET data from first set of   │  1002
│ PET data based on a plurality of phantom positions of a │
│ phantom, the first set of PET data being collected at   │
│ the plurality of phantom positions, and the second set  │
│ of PET data corresponding to one or more annihilation   │
│ events of the phantom                                   │
└─────────────────────────────────────────────────────────┘
                            │
                            ▼
┌─────────────────────────────────────────────────────────┐
│ Acquiring a first set of attenuation data for the       │  1004
│ phantom, the first set of attenuation data              │
│ corresponding to part of FOV of an imaging device       │
└─────────────────────────────────────────────────────────┘
                            │
                            ▼
┌─────────────────────────────────────────────────────────┐
│ Determining a second set of attenuation data for the    │  1006
│ phantom corresponding to the FOV of the imaging device  │
│ based on the plurality of phantom positions and the     │
│ first set of attenuation data                           │
└─────────────────────────────────────────────────────────┘
                            │
                            ▼
┌─────────────────────────────────────────────────────────┐
│ Reconstructing a PET image based on the second set of   │  1008
│ PET data and the second set of attenuation data         │
└─────────────────────────────────────────────────────────┘
```

```
Generating statistic data of phantom position by normalizing a     1102
plurality of phantom positions corresponding to FOV of an
               imaging device
```

```
Generating statistic data of nuclide decay by normalizing          1104
       nuclide decay corresponding to the FOV
```

```
Correcting the second set of PET data based on the statistic       1106
data of phantom position and the statistic data of nuclide decay
```

1500
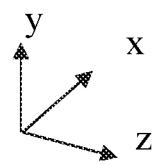
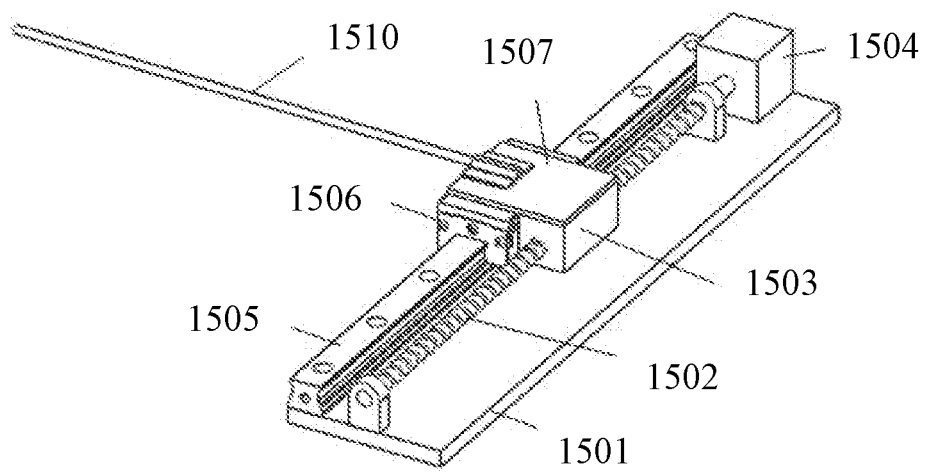
FIG. 15

1820

1820

METHOD AND SYSTEM FOR CALIBRATING AN IMAGING SYSTEM

CROSS-REFERENCE OF RELATED APPLICATIONS

This application is a continuation of U.S. application Ser. No. 17/156,708, filed on Jan. 25, 2021, which is a continuation of U.S. application Ser. No. 16/237,145 (issued as U.S. Pat. No. 10,902,646), filed on Dec. 31, 2018, which is a continuation of International Application No. PCT/CN2017/104779, filed on Sep. 30, 2017, which claims priority of Chinese Patent Application No. 201621099638.6, filed on Sep. 30, 2016, Chinese Patent Application No. 201611039000.8, filed on Nov. 21, 2016, and Chinese Patent Application No. 201710308861.X, filed on May 4, 2017. The entire contents of each of these applications are incorporated herein by reference.

TECHNICAL FIELD

The present disclosure generally relates to a medical system, and more specifically relates to methods and systems for calibrating a Positron Emission Tomography (PET) system.

BACKGROUND

Medical imaging systems may include a Positron Emission Tomography (PET) system for medical diagnosis or treatment. An object, such as a phantom, may be scanned to obtain PET data. During a performance test and a correction of the PET system, the phantom may be acquired to irradiate all detector units in the detector. For a PET system with a relatively long axial length (e.g., 2 meters), a plurality of phantoms may be used to perform the PET scan, based on which a PET image may be reconstructed. The inhomogeneity of the plurality of phantoms may introduce noise to the PET image. There is a need for a system and method to solve the problem.

SUMMARY

In a first aspect of the present disclosure, a method for medical imaging is provided. The method may include one or more of the following operations. A phantom may be moved along an axis of a scanner to a plurality of phantom positions. A first set of PET data relating to the phantom at the plurality of phantom positions may be acquired, by a scanner of the imaging device. The length of an axis of the phantom may be shorter than the length of an axis of the scanner, and at least one of the plurality of phantom positions may be inside a bore of the scanner. The first set of PET data may be stored as an electrical file.

In some embodiments, the plurality of phantom positions may be determined based on a scanning parameter of the scanner and a parameter of the phantom.

In some embodiments, the plurality of phantom positions may be determined based on at least one of scan time of the scanner, the length of the axis of the scanner, phantom weight and the length of the axis of the phantom.

In some embodiments, a PET image may be reconstructed at least based on the first set of PET data.

In some embodiments, a second set of PET data may be extracted from the first set of PET data based on the plurality of phantom positions of the phantom. The second set of PET data may correspond to one or more coincidence events of the phantom. A first set of attenuation data for the phantom may be acquired. The first set of attenuation data may correspond to part of the axis of the scanner. A second set of attenuation data for the phantom corresponding to the axis of the scanner may be determined based on the plurality of phantom positions and the first set of attenuation data. The PET image may be reconstructed based on the second set of PET data and the second set of attenuation data.

In some embodiments, calibration data may be acquired. The PET image may be corrected based on the plurality of phantom positions and the calibration data.

In some embodiments, statistic data of phantom position may be generated by normalizing the plurality of phantom positions. Statistic data of nuclide decay may be generated by normalizing nuclide decay corresponding to the axis of the scanner. The PET image may be corrected based on the statistic data of phantom position and the statistic data of nuclide decay.

In some embodiments, the phantom may be placed on a bed, and the motion controller may be configured to move the bed to drive the phantom to the plurality of phantom positions.

In a second aspect of the present disclosure, a system for medical imaging is provided. The system may include a bed configured to support a phantom, a scanner configured to detect coincidence events related to the phantom, and a motion controller configured to move the phantom along the scanner to a plurality of phantom positions. The system may include at least one storage medium and at least one processor. The at least one storage medium may include a set of instructions. The at least one processor may be configured to communicate with the at least one storage medium, wherein when executing the set of instructions, the system is configured to perform one or more of the following operations. A first set of PET data relating to a phantom at the plurality of phantom positions may be acquired, by the scanner of the imaging device. The length of an axis of the phantom may be shorter than the length of an axis of the scanner, and at least one of the plurality of phantom positions may be inside a bore of the scanner. The first set of PET data may be stored as an electrical file.

In some embodiments, the motion controller may be further configured to move the bed to drive the phantom to the plurality of phantom positions.

In some embodiments, the motion controller may include a first motion controller. The first motion controller may include a first moving mechanism and a second moving mechanism. The first moving mechanism may be configured to move the bed in a first direction or a second direction. The second moving mechanism may be configured to move the phantom in a third direction. The third direction may be perpendicular to the first direction and the second direction.

In some embodiments, the second moving mechanism may include a support plate, a first rotating wheel and a second rotating wheel, a first driver, and a transmission belt. The first rotating wheel and the second rotating wheel may be disposed at two ends of the support plate. The first driver may be connected to the first rotating wheel and the second rotating wheel. The transmission belt may encompass the first rotating wheel and the second rotating wheel. The transmission belt may extend in the third direction, and may be connected to the phantom.

In some embodiments, the second moving mechanism may include a support plate, a screw shaft, a second drive, and a support base. The screw shaft may be disposed on the support plate. The screw shaft may extend in the third direction. The second driver may be connected to an end of the screw shaft. The support base attached to the screw shaft. The support base may be connected to the phantom.

In some embodiments, the second moving mechanism may further include a guiding mechanism, and the phantom may be connected to and may move along the guiding mechanism.

In some embodiments, the second moving mechanism may further include a shield configured to shield radiation from the phantom.

In some embodiments, the motion controller may include a second motion controller. The second motion controller may include a moving mechanism. The moving mechanism may include a screw shaft, a slider block, and a shield. The screw shaft may extend along the first direction. An end of the screw shaft may be connected to a first driver. The slider block may be attached to the screw shaft. The slider block may be connected to the phantom. The shield may be configured to accommodate the screw shaft, the slider block and the phantom.

In some embodiments, the second motion controller may further include a rotation shaft, a second driver and a rotation arm. The second driver may be mounted on the slider block and may be connected to an end of the rotation shaft. The rotation arm may be configured to rotate the phantom under a force supplied by the rotation shaft.

In some embodiments, the shield may include a first shield comprising a first groove. The first groove may extend along the first direction, and the screw shaft may be disposed inside the first groove.

In some embodiments, the first groove may include a guiding mechanism. The slider block may be configured to move along the guiding mechanism.

In some embodiments, the shield may further include a second shield. A surface of the second field facing the phantom may include a second groove configured to provide a moving passage for the phantom. The second groove may extend in the first direction.

In some embodiments, the system may further include a third groove configured to accommodate the phantom. The third groove may be on a different plane from the second groove, and may extend in the first direction.

In some embodiments, the third groove may include two closed ends.

In a third aspect of the present disclosure, a non-transitory computer readable medium is provided. The non-transitory computer readable medium may include executable instructions that, when executed by at least one processor, cause the at least one processor to effectuate a method. The method may include one or more of the following operations. A first set of PET data relating to a phantom at a plurality of phantom positions may be acquired, by a scanner of the imaging device. The length of an axis of the phantom may be shorter than the length of an axis of the scanner, and at least one of the plurality of phantom positions may be inside a bore of the scanner. The first set of PET data may be stored as an electrical file.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 10 is a flowchart illustrating an exemplary process for processing PET data according to some embodiments of the present disclosure;

FIG. 11 is a flowchart illustrating an exemplary process for correcting the second set of PET data according to some embodiments of the present disclosure.

FIG. 15 is a schematic diagram illustrating a phantom controlling device according to another embodiment of the present disclosure;

DETAILED DESCRIPTION

Figure 1:
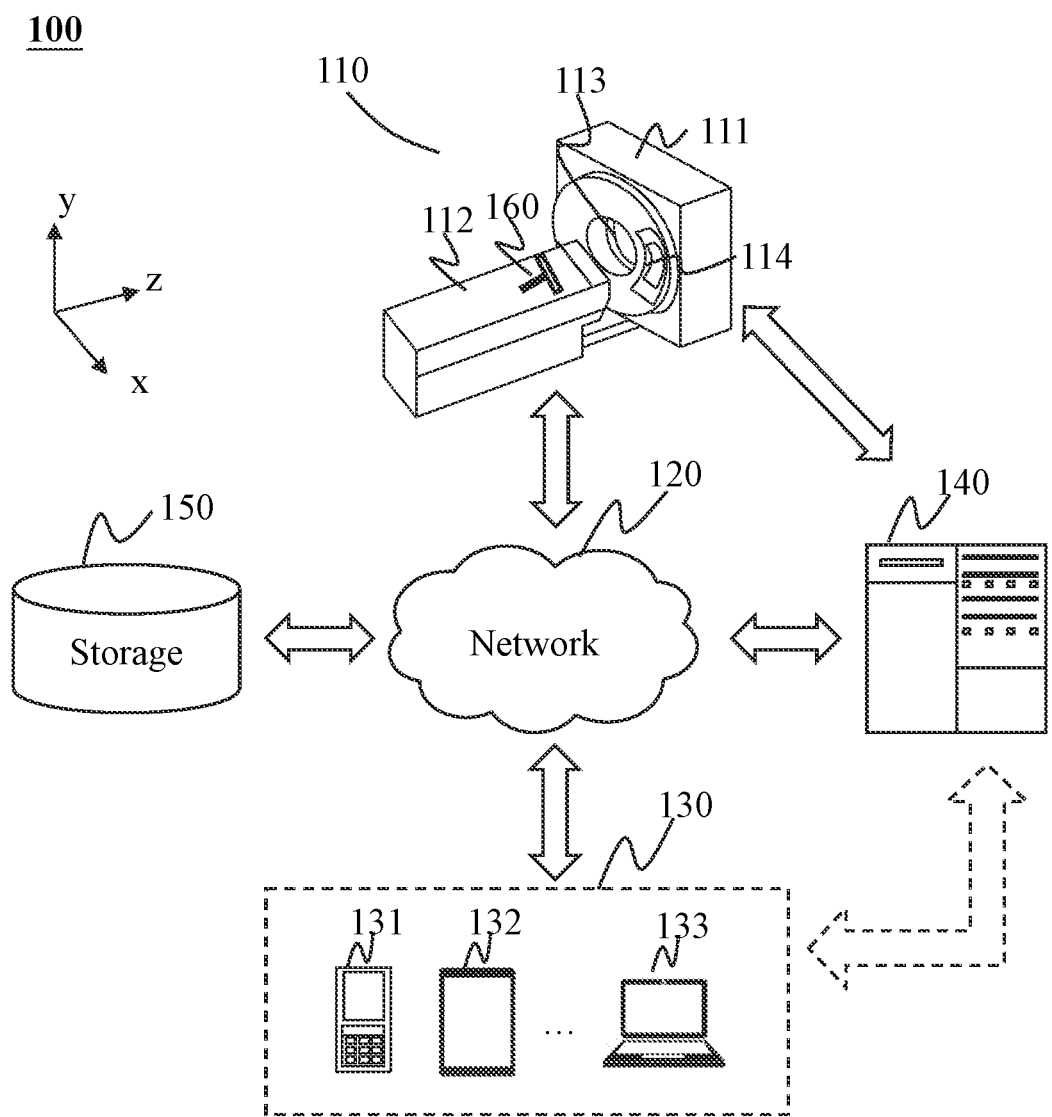
FIG. 1 is a schematic diagram illustrating an exemplary PET system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in descending order. However, the terms may be displaced by other expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein is a method and system for calibrating an imaging system (e.g., a PET system) and/or generating an image (e.g., a PET image). The present disclosure intends to calibrate the imaging system and/or generate the image with a phantom while being placed at a plurality of phantom positions. By placing the phantom in the plurality of phantom positions at a plurality of time nodes, which may imitate a plurality of phantoms being disposed at the plurality of phantom positions at a same time node, radiation related to the phantom may be utilized to calibrate the imaging system and/or generate the PET image, while sparing noise that may be introduced due to the inhomogeneity of the plurality of phantoms.

The term "image" used in this disclosure may refer to a 2D image, a 3D image, a 4D image, and/or any related data (e.g., PET data, radiation data corresponding to the PET data). This is not intended to limit the scope of the present disclosure. For persons having ordinary skills in the art, a certain amount of variations, changes, and/or modifications may be deducted under the guidance of the present disclosure.

The term "radiation" used herein may include a particle radiation, a photon radiation, or the like, or any combination thereof. The particle may include a positron, a neutron, a proton, an electron, a µ-meson, a heavy ion, or the like, or any combination thereof. The photon may include a gamma photon, an, a beta photon, an X-ray photon, or the like, or any combination thereof. Those variations, changes, and/or modifications do not depart from the scope of the present disclosure.

FIG. 1 is a schematic diagram illustrating an exemplary PET system 100 according to some embodiments of the present disclosure. As shown, the PET system 100 may include a PET scanner 110, a network 120, one or more terminals 130, a processing engine 140, a storage 150, and a motion controller 160.

The PET scanner 110 may include a gantry 111, a bed 112 (or referred to as a scanning table 112), a detecting region 113, and a detector 114. The detector 114 may be mounted on the gantry 111. The bed 112 may be positioned within a bore of the gantry 111. Specifically, the bed 112 may be adapted to be accommodated in a bore enclosed by a plurality of detector units of the detector 114 mounted on the gantry 111.

The bed 112 may support an object (e.g., a phantom) for scanning. The object (e.g., a phantom) may include a radioactive source that may emit radiology rays. The radiology rays emitted by the phantom may be detected by one or more detector units of the detector 114. When an object is supported by a bed 112, the bed 112 may be at a bed location. Merely by way of example, a bed location may be described as a location of the bed 112 relative to the gantry 111 of the PET system 100 in a certain direction. The certain direction may include, for example, an X direction, a Y direction, and/or a Z direction. As used herein, the X direction, the Y direction, and the Z direction may represent an X axis, a Y axis, and a Z axis in a coordinate system. Merely by way of example, the X axis and the Z axis may be in a horizontal plane, the X axis and the Y axis may be in a vertical plane, the Z axis may be along the rotational axis of the PET scanner 110. The phantom supported by the bed 112 may be at a phantom position. The phantom position may be described as a spatial location of the phantom relative to the gantry 111 of the PET system 100 in a certain direction. The certain direction may include, for example, an X direction, a Y direction, and/or a Z direction as illustrated elsewhere in the present disclosure. In some embodiments, the phantom may be placed at a plurality of phantom positions. The plurality of phantom positions may be expressed as below:

{phantom position 1, phantom position 2, . . . , phantom position i, . . . , and phantom position N}

In some embodiments, the phantom may be fixed on the bed 112, and a phantom position may correspond to a bed position. In some embodiments, when the bed 112 stops at a bed position, the phantom may be moved on the bed 112 to stop at a plurality of phantom positions for imaging. Therefore, a bed position may correspond to a plurality of phantom positions.

The detector 114 may detect or collect PET data relating to photons. The photons may include a gamma photon, an x-ray photon, or the like, or any combination thereof. The PET data may include, for example, scanning data related to the object being scanned (e.g., the phantom). The scanning data may include, for example, a plurality of coincidence events detected by the detector 114 and/or line of response (LOR)s corresponding to the plurality of coincidence events. As used herein, an LOR may refer to a line connecting the detector units that have detected two photons of a coincidence event. Merely by way of example, the detector 114 may collect a first set of PET data. The first set of PET data may refer to original PET data (e.g., counting response of the detector 114) collected by the scanner. In some embodiments, the phantom may be placed at a plurality of phantom positions to generate the first set of PET data. For example, the first set of PET data may include a plurality sub-sets of PET data, which may be generated by the phantom at a plurality of phantom positions respectively. The plurality sub-sets of PET data may be expressed as below:

{PET data 1, PET data 2, . . . , PET data i, . . . , and PET data N} wherein each sub-set of PET data of the plurality sub-sets of PET data may correspond to a phantom position of the plurality of phantom positions. Merely by way of example, PET data 1 may correspond to phantom position 1, PET data may correspond to phantom position 2, PET data i may correspond to phantom position i, etc. I or N may represent an interger larger than 1.

In some embodiments, at least a portion of the first set of PET data (also referred to as a second set of PET data) may correspond to one or more coincidence events of the phantom. The second set of PET data may be extracted from the first set of PET data. The detailed description of extracting the second set of PET data may be found in FIG. 6 in the present disclosure and the description thereof.

In some embodiments, the detector 114 may include one or more detector units for detecting scanning data relating to an object (e.g., a phantom), or a portion thereof, located in the detecting region 113. A detector unit may include a scintillation detector 114 (e.g., a cesium iodide detector 114), a gas detector 114, etc. The detector 114 may be and/or include a single-row detector 114 and/or a multi-row detector 114. In some embodiments, the detector 114 may further send the detected PET data to the processing engine 140.

The network 120 may include any suitable network that can facilitate exchange of information and/or data (e.g., emission data) for the PET system 100.

In some embodiments, one or more components of the PET system 100 (e.g., the PET scanner 110, the terminal 130, the processing engine 140, the storage 150, etc.) may communicate information and/or data with one or more other components of the PET system 100 via the network 120. For example, the processing engine 140 may obtain emission data from the PET scanner 110 via the network 120. As another example, the processing engine 140 may obtain user instructions from the terminal 130 via the network 120.

The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the PET system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™ etc. In some embodiments, the terminal(s) 130 may be part of the processing engine 140.

The processing engine 140 may process data and/or information obtained from the PET scanner 110, the terminal 130, and/or the storage 150. Merely by way of example, the processing engine 140 may process the emission data (e.g., the reference emission data, the working emission data, etc.) transmitted from the detector 114 of the PET scanner 110.

In some embodiments, the processing engine 140 may be a single server or a server group. The server group may be centralized or distributed. In some embodiments, the processing engine 140 may be local or remote. For example, the processing engine 140 may access information and/or data stored in the PET scanner 110, the terminal 130, and/or the storage 150 via the network 120. As another example, the processing engine 140 may be directly connected to the PET scanner 110, the terminal 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage 150 may store data, instructions, and/or any other information. In some embodiments, the storage 150 may store data obtained from the terminal 130 and/or the processing engine 140. In some embodiments, the storage 150 may store data and/or instructions that the processing engine 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the PET system 100 (e.g., the processing engine 140, the terminal 130, etc.). One or more components in the PET system 100 may access the data or instructions stored in the storage 150 via the network 120. In some embodiments, the storage 150 may be directly connected to or communicate with one or more other components in the PET system 100 (e.g., the processing engine 140, the terminal 130, etc.). In some embodiments, the storage 150 may be part of the processing engine 140.

The motion controller 160 may move the phantom to a plurality of phantom positions. The motion controller 160 may move the phantom to the plurality of phantom positions directly. For example, the phantom may connect to a motion controller 160 placed on the bed 112. The motion controller 160 may move the phantom directly on the bed 112. The motion controller 160 may move the phantom to the plurality of phantom positions indirectly. For example, the bed 112 may connect to a motion controller 160, and the motion controller 160 may move the bed 112 to a plurality of positions in a certain direction (e.g., the X direction, the Y direction, and/or the Z direction). Accordingly, the phantom being placed on the bed 112 may be moved to a plurality of positions in the certain direction (e.g., the X direction, the Y direction, and/or the Z direction).

The motion controller 160 may be of various configurations. For example, the motion controller 160 may include a first motion controller and/or a second motion controller. The first motion controller may move the bed 112 and/or the phantom in one or more certain directions. Merely by way of example, the first motion controller may include a first moving mechanism and a second moving mechanism. The first moving mechanism (or referred to as a scanning-table driving mechanism) may be configured to move the bed 112 in a first direction (e.g., the Z direction) or a second direction (e.g., the Y direction). The second moving mechanism (or referred to as phantom controlling device) may be configured to move the phantom in a third direction (e.g., the Y direction) perpendicular to the first direction and the second direction. The second motion controller may move the phantom in a one or more certain directions (e.g., the Z direction). Exemplary first motion controller, first moving mechanism, second moving mechanism, may be found in FIGS. 13-17 and the description thereof. Exemplary second motion controller may be found in FIG. 18 and the description thereof.

Figure 2:
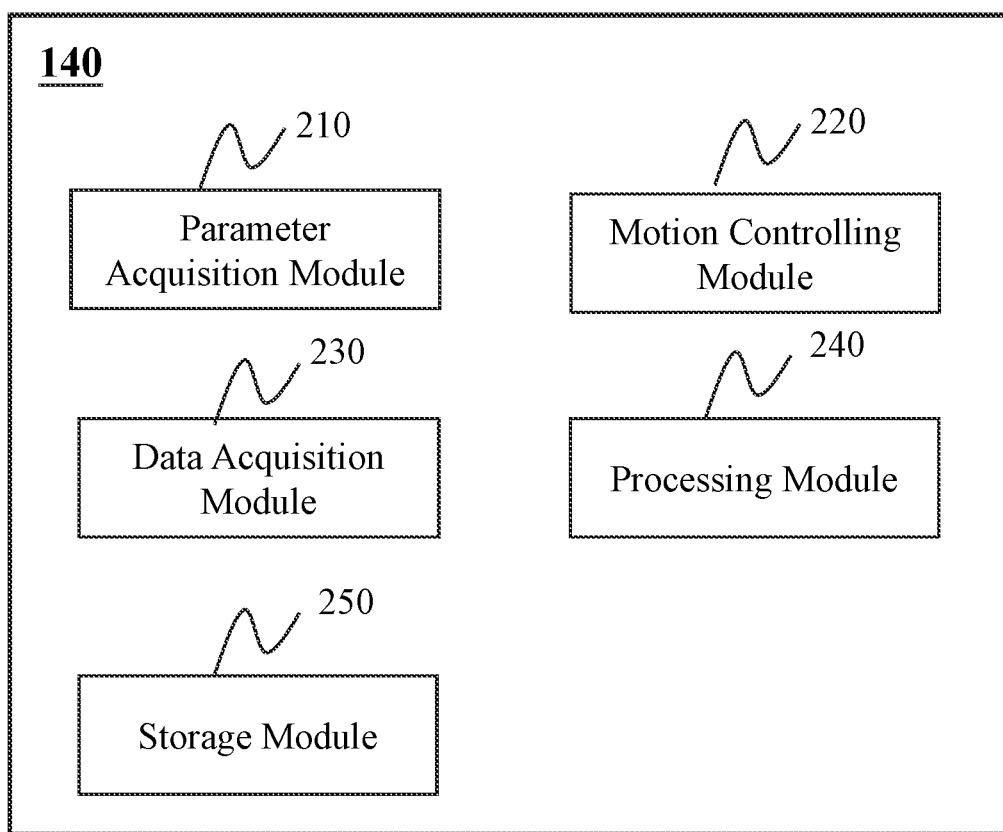
FIG. 2 is a block diagram illustrating an exemplary processing engine according to some embodiments of the present disclosure.

FIG. 2 is a block diagram illustrating an exemplary processing engine 140 according to some embodiments of the present disclosure. As illustrated in FIG. 2, the processing engine 140 may include a parameter acquisition module 210, a motion controlling module 220, a data acquisition module 230, a processing module 240, and a storage module 250.

The parameter acquisition module 210 may acquire at least one of a scanning parameter of a scanner (e.g., the scanner of the PET system 100) or a parameter of a phantom from one or more components in the PET system 100 (e.g., the PET scanner 110, the network 120, the terminal 130, and/or the storage 150). The scanning parameter may be configured to scan a phantom and different configurations of the scanning parameter may cause different results of the scanning of a phantom. In some embodiments, the scanning parameter may be related to the size or structure of a scanner (e.g., the PET scanner 110 of the PET system 100). For example, the scanning parameter may include the length of the axis of the scanner. In some embodiments, the scanning parameter may be designated by a user (e.g., a doctor, a nurse, a patient, etc.). For example, the scanning parameter of the scanner may include scan time of the scanner. A parameter of the phantom may include phantom weight, the length of the axis of the phantom, the size of the phantom, etc.

The parameter acquisition module 210 may connect to or communicate with the motion controlling module 220, and transmit the acquired parameter (e.g., the scanning parameter of the scanner, or the parameter of the phantom) thereto.

The motion controlling module 220 may determine a plurality of phantom positions and/or generate a motion instruction to control the movement of the phantom and/or the bed 112.

The motion controlling module 220 may determine a plurality of phantom positions. In some embodiments, the motion controlling module 220 may determine the plurality of phantom positions based on the scanning parameter of the scanner and/or the parameter of the phantom. Merely by way of example, the motion controlling module 220 may determine the plurality of phantom positions based on scan time of the scanner, the length of the axis of the scanner, phantom weight or the length of the axis of the phantom. The determined plurality of phantom positions may be expressed as below:

{phantom position 1, phantom position 2, . . . , phantom position i, . . . , and phantom position N}

In some embodiments, the plurality of the phantom positions may ensure that the axis of the scanner is completely covered by the phantom while being placed in the plurality of phantom positions. Therefore, the scintillator crystals in the detector 114 may be irradiated by the phantom while being placed in the plurality of phantom positions (e.g., radiation rays generated by the phantom). For example, the plurality of phantom positions may include a phantom position 1 and a phantom position 2. When the phantom is placed in the phantom position 1, a first set of scintillator crystals corresponding to a first part of the axis of the scanner may be irradiated by radiation rays generated by the phantom. When the phantom is placed in the phantom position 2, a second set of scintillator crystals corresponding to a second part of the axis of the scanner may be irradiated by radiation rays generated by the phantom. The first set of scintillator crystals and at least part of the second set of scintillator crystals may constitute all the scintillator crystals in the detector 114. The first part of the axis of the scanner and at least part of the second part of the axis of the scanner may correspond to the entire axis of the PET scanner 110. Thus, while placing the phantom in the phantom positon 1 and the phantom position 2, the phantom may cover the axis of the scanner, and the scintillator crystals in the detector 114 may be irradiated by radiation rays generated by the phantom at the phantom position 1 and the phantom position 2.

The motion controlling module 220 may generate a motion instruction to control the movement of the phantom and/or the bed 112. As used herein, a movement of the phantom (or the bed 112) may be represented by one or more parameters, for example, a velocity of the phantom (or the bed 112), an accelerated velocity of the phantom (or the bed 112), a moving direction of the phantom (or the bed 112), a moving time span of the phantom (or the bed 112), a moving range of the phantom (or the bed 112), an acceleration range of the phantom (or the bed 112), a deceleration range of the phantom (or the bed 112), or the like, or a combination thereof. In some embodiments, the motion controlling module 220 may generate the motion instruction based on a user command. The user command may be input by the user through, for example, the terminal 130.

The motion controlling module 220 may connect to or communicate with the motion controller 160 or the data acquisition module 230. For example, the motion controlling module 220 may transmit the determined plurality of phantom positions to the data acquisition module 230. As another example, the motion controlling module 220 may transmit the generated motion instruction to the motion controller 160, which may operate according to the motion instruction.

The data acquisition module 230 may acquire data and/or information from the motion controller 160 and one or more components in the PET system 100 (e.g., the PET scanner 110, the network 120, the terminal 130, the processing engine 140, and/or the storage 150). The data and/or information acquired may include the determined plurality of phantom positions, a first set of PET data, and correction data.

The first set of PET data may refer to original PET data collected by the scanner. The original PET data may include counting response of the detector 114. In some embodiments, the first set of PET data may correspond to the plurality of phantom positions determined by the motion controlling module 220.

The correction data may be configured to correct a PET image related to the phantom and/or determine a factor of the detector 114. Merely by way of example, the correction data may include counting response of each scintillator crystal of the detector 114, based on which a normalizing factor for normalizing the detecting efficiency of the detector 114 may be determined. The counting response of the detector 114 may be determined by placing the phantom in a plurality of phantom positions. As another example, the correction data may include a first set of attenuation data for the phantom, based on which a PET image related to the phantom may be corrected. As used herein, the first set of attenuation data for the phantom may refer to attenuation data corresponding to part of the field of vision (FOV) of the PET system 100. The attenuation data may include an attenuation map generated from the CT scan data of the phantom. Further, as another example, the correction data may include nuclide decay information for the phantom, based on which a PET image related to the phantom may be corrected.

The data acquisition module 230 may transmit the acquired data and/or information to the motion controlling module 220, the processing module 240, and/or the storage module 250. In some embodiments, the data acquisition module 230 may transmit the plurality of phantom positions, the first set of PET data, and the correction data to the processing module 240. Specifically, for example, the data acquisition module 230 may transmit the acquired first set of PET data, the plurality of phantom positions, and/or the first set of attenuation data for the phantom to the PET image reconstruction unit 241 (shown in FIG. 7) in the processing module 240. As another example, the data acquisition module 230 may transmit the plurality of phantom positions and the nuclide decay information for the phantom to the correction unit 242 (shown in FIG. 7) in the processing engine 140.

The processing module 240 may process information provided by the data acquisition module 230. In some embodiments, the processing module 240 may reconstruct PET images based on the first set of PET data, the plurality of phantom positions, and/or the first set of attenuation data for the phantom according to a reconstruction algorithm, determine a normalizing factor of the detector 114, and/or perform any other function for image reconstruction in accordance with various embodiments of the present disclosure. The reconstruction algorithm may include an ML-EM (Maximum Likelihood Expectation Maximization), an OSEM (Ordered Subset Expectation Maximization), a RAMLA (Row-Action Maximum Likelihood Algorithm), a DRAMA (Dynamic Row-Action Maximum Likelihood Algorithm), or the like, or a combination thereof.

The storage module 250 may store PET data, control parameters, processed PET data, or the like, or a combination thereof. For example, the storage module 250 may store the algorithms to be employed by the processing module 240. As another example, the storage module 250 may store the first set of PET data acquired from the data acquisition module 230. In some embodiments, the storage may store one or more programs and/or instructions that may be executed by the processor(s) of the processing engine 140 to perform exemplary methods described in this disclosure. For example, the storage may store program(s) and/or instruction(s) that can be executed by the processor(s) of the processing engine 140 to cause the PET system 100 or a portion thereof to acquire PET data and/or to process the PET data, etc. In some embodiments, the storage module 250 may include a mass storage. For example, the mass storage may include a magnetic disk, an optical disk, a solid-state drives, etc.

It should be noted that the above description of the processing engine 140 is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure. For example, the parameter acquisition module 210 and the data acquisition module 230 may be integrated to a data acquisition module 230, which perform the function of both the parameter acquisition module 210 and the data acquisition module 230.

Figure 3:
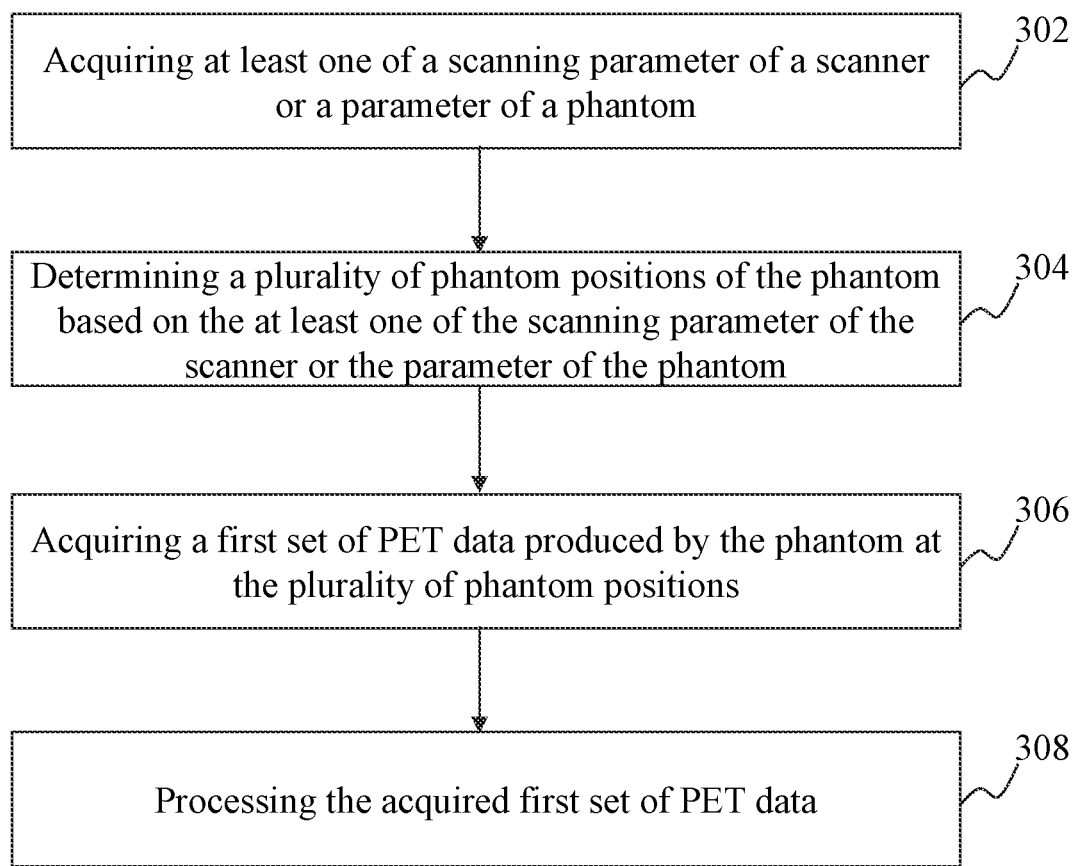
FIG. 3 is a flowchart illustrating an exemplary process for processing PET data according to some embodiments of the present disclosure.

FIG. 3 is a flowchart illustrating an exemplary process 300 for processing PET data according to some embodiments of the present disclosure. The process, or a portion thereof, may be implemented on a processing engine 140 as illustrated in FIG. 1. For illustration purposes, the following description is provided with reference to the PET system 100 as illustrated in FIG. 1. As already described, the PET system 100 includes a detector 114 including scintillator crystals.

In 302, the parameter acquisition module 210 may acquire at least one of a scanning parameter of a scanner or a parameter of a phantom. The scanning parameter may be configured to scan a phantom and different configurations of the scanning parameter may cause different results of the scanning of a phantom. For example, the scanning parameter may include the length of the axis of the scanner, scan time of the scanner, etc. The parameter of the phantom may include phantom weight, the length of the axis of the phantom, the size of the phantom, etc.

In 304, the motion controlling module 220 may determine a plurality of phantom positions based on the at least one of the scanning parameter of the scanner or the parameter of the phantom. Merely by way of example, the motion controlling module 220 may determine the plurality of phantom positions based on scan time of the scanner, the length of the axis of the scanner, phantom weight or the length of the axis of the phantom. The determined plurality of phantom positions may be expressed as: {phantom position 1, phantom position 2, . . . , phantom position i, . . . , and phantom position N}. In some embodiments, the determined plurality of the phantom positions may ensure that the axis of the scanner is completely covered by the phantom while being placed in the plurality of phantom positions. Therefore, the scintillator crystals in the detector 114 maybe irradiated by the phantom (e.g., radiation rays generated by the phantom) while being placed in the plurality of phantom positions.

In 306, the data acquisition module 230 may acquire a first set of PET data produced by the phantom at the plurality of phantom positions. The first set of PET data may refer to a set of original PET data collected by the scanner while the phantom is placed at the plurality of phantom positions. The set of original PET data may include a plurality of sub-sets of PET data, which may be generated by the phantom at the plurality of phantom positions respectively. The plurality sub-sets of PET data may be expressed as: {PET data 1, PET data 2, . . . , PET data i, . . . , and PET data N}.

In 308, the processing module 240 may process the acquired first set of PET data. In some embodiments, the processing module 240 may process the acquired first set of PET data (e.g., the PET data 1, the PET data 2, etc.) corresponding to the respective phantom positions (e.g., the phantom position 1, the phantom position 2, etc.) to generate a PET image. In some embodiments, the processing module 240 may process the acquired first set of PET data to determine normalizing factors of a detector 114. For example, the acquired first set of PET data may include counting responses (e.g., a first counting response, a second counting response, an ith counting response, an nth counting response, etc.) of scintillator crystals (e.g., a first scintillator crystal, a second scintillator crystal, an ith scintillator crystal, an nth scintillator crystal, etc.) of the detector 114. The normalizing factor of a certain scintillator crystal may be determined based on the counting response of the scintillator crystal. For example, the normalizing factor of the ith scintillator crystal Mi may be determined by:

$$M_i = \frac{\sum_i^M D_i / M}{D_i}, \tag{1}$$

wherein M may represent the number of the scintillator crystals, Di may represent the counting response of the ith scintillator crystal, and i may represent an integer larger than 1.

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, a step in which the first set of PET data may be stored may be added between operation 306 and 308.

Figure 4A:
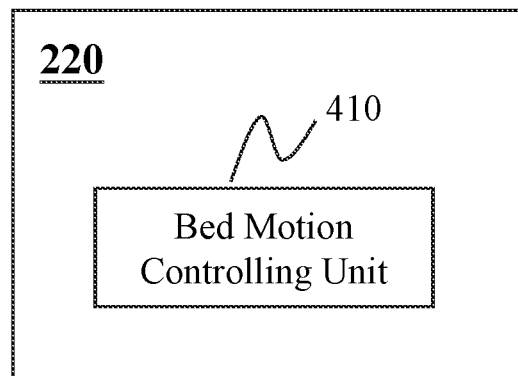
FIG. 4A is a block diagram illustrating an exemplary motion controlling module according to some embodiments of the present disclosure.

FIG. 4A is a block diagram illustrating an exemplary motion controlling module 220 according to some embodiments of the present disclosure. As illustrated, the motion controlling module 220 may include a bed motion controlling unit 410.

The bed motion controlling unit 410 may control the movement of the scanning table 112 (or referred to as the bed 112) and adjust the position of the scanning table 112 in real time. For example, the bed motion controlling unit 410 may drive the scanning table 112 to move along the rotational axis of the PET scanner 110.

In some embodiments, the bed motion controlling unit 410 may control the movement of the scanning table 112 based on the scanning parameters of the PET scanner 110, the information of the phantom and/or the information of the scanning table 112. Specifically, the bed motion controlling unit 410 may perform logical calculations based on the acquired scanning parameters of the PET scanner 110, the information of the phantom and/or the information of the scanning table 112 to obtain motion control logic of the scanning table 112. The motion control logic of the scanning table 112 may relate to, for example, a movement range of the scanning table 112 along the axis (Z direction) of the detector 114, a movement speed of the scanning table 112 and acceleration/deceleration positions of the scanning table 112. As used herein, an acceleration position of the scanning table 112 may relate to location at which the scanning table 112 starts to accelerate. A deceleration position of the scanning table 112 may relate to location at which the scanning table 112 starts to decelerate. In some embodiments, to ensure the detector 114 to collect enough phantom data (or referred to as scanning data related to the phantom), the scanning time of the PET system 100 to the phantom may be increased, the scanning table 112 may perform reciprocating motions. The number of times of reciprocating motion of the scanning table 112 may be adjusted and controlled by the motion control logic of the scanning table 112, which is calculated by the bed motion controlling unit 410. It should be noted that the bed motion controlling unit 410 may control the scanning table 112 to move continuously during a certain time interval or move at a uniform velocity. The bed motion controlling unit 410 may also control the scanning table 112 to move dis-continuously during at least one certain time interval or at a non-uniform velocity. It may be within the intent of the present disclosure to control the movement of the scanning table 112 during the scanning process, to ensure predetermined detector units to detect the phantom (or the scanning data related to the phantom). As used herein, the predetermined detector units may refer to one or more detector units of which the detecting abilities are to be tested. The predetermined detector units may be designated by a user or the PET system 100. The predetermined detector units may include one or more detector units. For example the predetermined detector units may include all detector units of the detector 114.

Figure 4B:
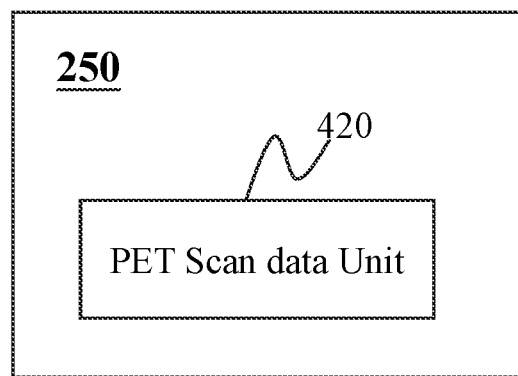
FIG. 4B is a block diagram illustrating an exemplary storage module according to some embodiments of the present disclosure.

FIG. 4B is a block diagram illustrating an exemplary storage module 250 according to some embodiments of the present disclosure. As illustrated, the storage module 250 may include a PET scan data unit 420. The PET scan data unit 420 may store the scanning data related to the phantom, the position information of the scanning table 112, and/or the position or length information of the phantom.

Figure 5:
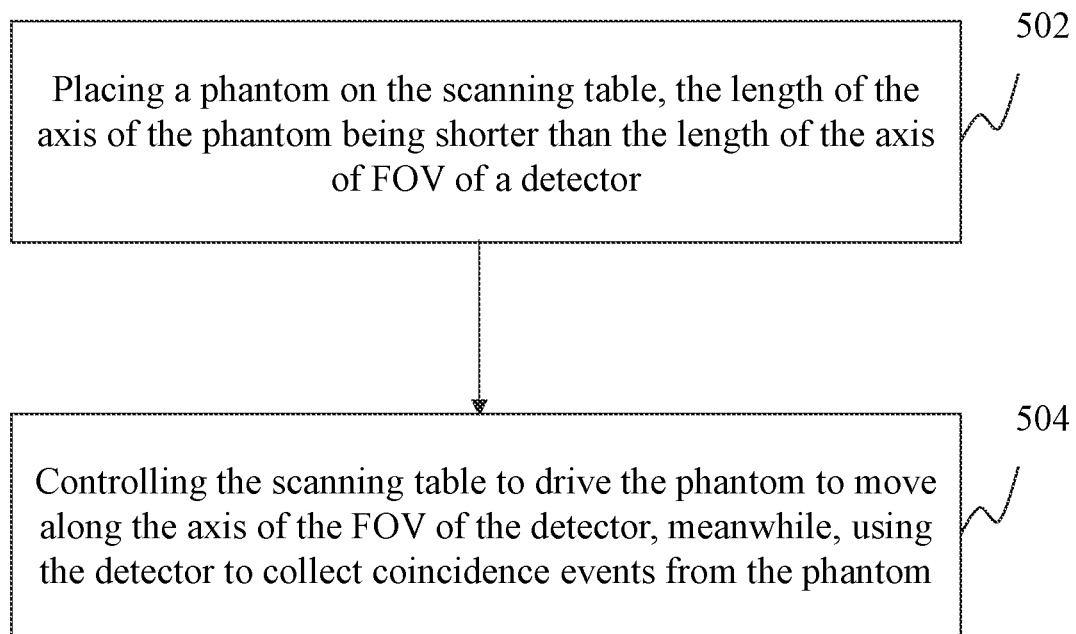
FIG. 5 is a flowchart illustrating a method for collecting PET data according to some embodiments of the present disclosure.

FIG. 5 is a flowchart illustrating a method for collecting PET data (or referred to as a PET data collection method) according to some embodiments of the present disclosure. As shown in FIG. 5, the method may include one or more steps as illustrated below.

In 502, a phantom may be placed on the scanning table 112, and the length of the axis of the phantom may be shorter than the length of the axis of FOV of the detector 114.

In 504, the scanning table 112 may be controlled to drive the phantom to move along the axis of FOV of the detector 114. Meanwhile, the detector 114 may be used to collect coincidence events from the phantom.

In the PET data collection method according to the present disclosure, the predetermined detector units may be irradiated by the phantom by controlling a movement of the scanning table 112 during the collection related to the phantom. When the predetermined detector units include all the detector units of the detector 114, the collected data by all the detector units of the detector 114 may be used to determine a normalizing factor and generate a reconstructed PET image. Thus, in the PET data collection method according to the present disclosure, by controlling the movement of the scanning table 112, most of the axial FOV, or even entire axial FOV of the detector 114 may be covered by a short phantom (e.g., a phantom with an axis shorter than the axis of the PET scanner 110). In conclusion, via the PET data collection method according to the present disclosure, a phantom (the length of the axis of the phantom may be shorter than the length of the axis of FOV of the detector 114) may be used to facilitate the predetermined detector units in the detector 114 and even all detector units to collect data of the phantom.

With the scanning method according to the present disclosure, for the long axial PET system 100, a single phantom with an axial length shorter than the axial length of FOV of the detector 114 may be used to facilitate the predetermined detector units to collect data of the phantom and ensure the radiation uniformity of the phantom.

Further, data obtained by the scanning method of a PET system 100 according to the present disclosure may be applied to a PET image reconstruction. The reconstructed PET image may further be used to analyze the PET system 100. The data obtained by the scanning method according to the present disclosure may be utilized to generate the normalizing factor of the detector efficiency.

Figure 6:
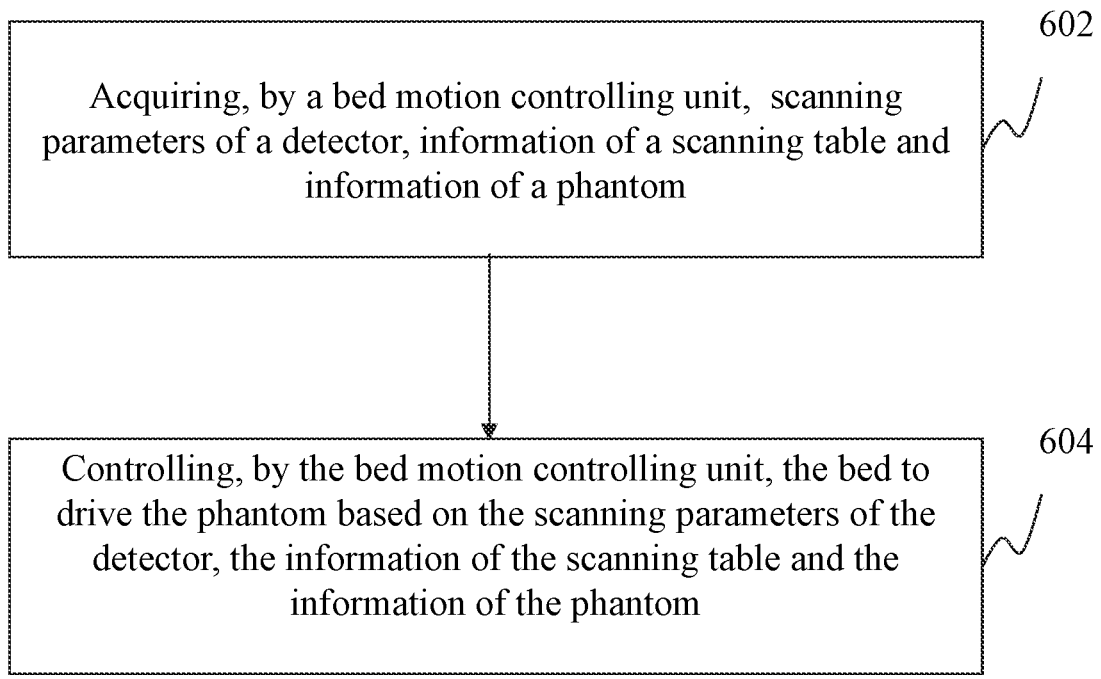
FIG. 6 is a flowchart illustrating a method for collecting PET data according to some embodiments of the present disclosure.

FIG. 6 is a diagram illustrating a method for collecting PET data according to an embodiment of the present disclosure. The scanning method of the PET system 100, in some embodiments will be further described below in combination with FIG. 1, FIG. 3 and FIG. 6.

In step 502, a phantom may be placed on the scanning table 112 and the length of the axis of the phantom may be shorter than the length of the axis of FOV of the detector 114.

Referring to FIG. 1, the PET system 100 may include a detector 114 and a scanning table 112. During a scan of the PET system 100, the phantom may be placed on the scanning table 112. With a movement of the scanning table 112, the phantom may be moved into the FOV of the detector 114 so that the phantom may be scanned by the detector 114 to collect coincidence events generated from the phantom. Further, the detector 114 may include a plurality of detector units arranged in a circular shape. The coincidence events within the FOV of the detector 114 may be detected by the plurality of detector units 111.

In step 504, the scanning table 112 may be controlled to drive the phantom to move along the axis of FOV of the detector 114. Meanwhile, the detector unit may be used to collect coincidence events from the phantom. Thus, during the data collection process, the phantom may be moved along the axis to ensure that the predetermined detector units are irradiated by the phantom.

Further, when the scanning table 112 is controlled to move with the phantom along the axis of the PET scanner 110, the movement of the scanning table 112 may be specifically controlled based on scanning parameters of the PET scanner 110. The scanning parameters of the PET scanner 110 may include a scanning time and/or the length of the axis of FOV of the detector 114 (e.g., the Z direction shown in FIG. 1). Further, when the scanning table 112 is controlled to move with the phantom along the axis of the PET scanner 110, the scanning table 112 may also be controlled to move with the phantom based on information of the phantom. The information of the phantom may include the length, position and weight of the phantom, etc. Specifically, the information of the phantom may be obtained by a Computed Tomography (CT) image of the phantom. The CT image of the phantom may be obtained by CT scanning of the phantom.

The phantom may be placed on the scanning table 112 and may be moved along with the movement of the scanning table 112. When the scanning table 112 is controlled to move with the phantom along the axis of the PET scanner 110, information of the scanning table 112 may be further combined to control the movement of the phantom along the axis of the PET scanner 110 (e.g., the Z direction shown in FIG. 1) and along a direction perpendicular to the axis (e.g., the Y direction shown in FIG. 1). In some embodiments, the information of the scanning table 112 may be a deformation factor of the scanning table 112 estimated by a deformation curve of the scanning table 112. Specifically, the deformation factor of the scanning table 112 may include the deformation factor of the scanning table 112 in the height direction, the direction perpendicular to the ground floor (e.g., the Y direction shown in FIG. 1). It may be possible to adjust the height position of the scanning table 112 in real time by applying the deformation factor of the scanning table 112 to the height direction. In some embodiments, the height position of the scanning table 112 may be adjusted dynamically in a manner to ensure that the phantom (or a certain point of the phantom) moves along the axis of the PET scanner (e.g., the Z direction shown in FIG. 1).

During the scanning of the phantom by the detector 114, the movement of the scanning table 112 may be controlled. In some embodiments, the scanning table 112 may be moved to a plurality of bed positions. As a result, the phantom placed on the scanning table 112 may be moved to a plurality of phantom positions. Thus, for a PET system 100 with a long axial length, the predetermined detector units may be irradiated respectively by a short phantom (e.g., a phantom with an axis shorter than the length of the axial FOV of the detector 114) placed at the plurality of phantom positions. In some embodiments, most or all of the detector units in the detector 114 may be irradiated when scanning with a short phantom at the plurality of phantom positions to ensure that the phantom cover most of the axial FOV (e.g., 80%) or even the entire axial FOV of the detector 114.

As described above, when the movement range of the phantom along the axis of the PET scanner 110 corresponds to an axial length larger than or equal to the length of the axis of FOV of the detector 114, the irritation of phantom may completely cover the entire axial FOV of the detector 114, and thus, all detector units of the detector 114 may collect data of the phantom. In some embodiments, the data collected by the detector units (e.g., all detector units of the detector 114) may be further used for the normalization correction (e.g., determining a normalizing factor) or PET image reconstruction. In addition, since all detector units collect data based on a uniform phantom rather than a phantom formed by splicing, for example, a few sub-phantoms, the coincidence events detected by all detector units are statistically the same. Therefore, a more accurate normalizing factor and a more accurate reconstructed PET image may be obtained, compared with that generated with a phantom that is spliced by a few sub-phantoms. As a result, the performance of the PET system 100 may be tested and the PET system 100 may be corrected more accurately.

Figure 7:
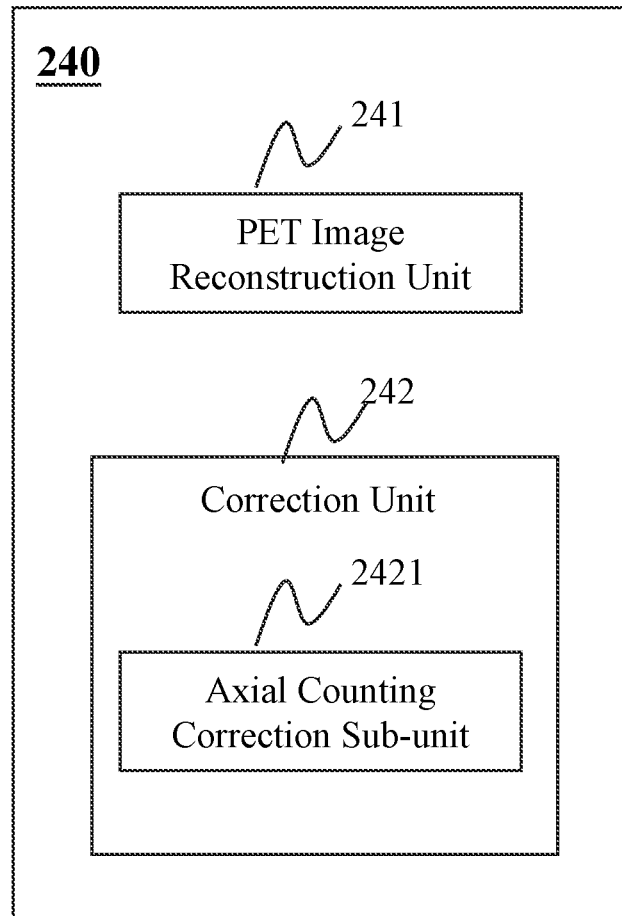
FIG. 7 is a block diagram illustrating an exemplary processing module according to some embodiments of the present disclosure.

FIG. 7 is a block diagram illustrating an exemplary processing module 240 according to some embodiments of the present disclosure. As shown, the processing module 240 may include a PET image reconstruction unit 241 and a correction unit 242. The correction unit 242 may include an axial counting correction sub-unit 2421.

The PET image reconstruction unit 241 may be configure to reconstruct a PET image based on the coincidence events detected by the detector units. The PET image reconstruction unit 241 may reconstruct a PET image based on the first set of PET data, the plurality of phantom positions, and/or the first set of attenuation data for the phantom acquired from the data acquisition module 230. Merely by way of example, the PET image reconstruction unit 241 may be used to extract valid scanning data based on position of the phantom and to reconstruct PET image in conjunction with attenuation information for the phantom within the entire axial FOV. In some embodiments, the PET image reconstruction unit 241 may transmit the generated PET image to the correction unit 242.

The correction unit 242 may correct the generated PET image and/or determine a normalizing factor based on correction data (e.g., first set of attenuation data for the phantom, counting response of each scintillator crystal of the detector 114, and the nuclide decay information for the phantom) and the plurality of phantom positions from the data acquisition module 230. For example, the correction unit 242 may correct the reconstructed PET image based on the plurality of phantom positions and the nuclide decay information for the phantom. To correct the reconstructed PET image, the correction unit 242 may generate statistic data of phantom position by normalizing a plurality of phantom positions, generate statistic data of nuclide decay by normalizing nuclide decay, and further correct the PET image based on the statistic data of phantom position and the statistic data of nuclide decay. The plurality of phantom positions and the nuclide decay may correspond to the FOV of the detector 114. As another example, the correction unit 242 may correct the reconstructed PET image based on the first set of attenuation data for the phantom and the plurality of phantom positions. As another example, the correction unit 242 may determine a normalizing factor for normalizing the detecting efficiency of the detector 114 based on the counting response of each scintillator crystal of the detector 114. The correction unit 242 may correct an axial count of the detector 114. For example, as illustrated, the correction unit 242 may include an axial counting correction sub-unit 2421. The axial counting correction sub-unit 2421 may be used to perform an axial count correction based on statistic information about the scanning table position and statistic information about the nuclide decay within the axial FOV, in conjunction with the reconstructed PET image, to improve the image deviation that may be caused by the movement of the scanning table 112 and the nuclide decay.

It should be noted that the above description of the processing module 240 is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure. For example, the correction unit 242 may be omitted and the function of the correction unit 242 may be realized by the image reconstruction unit.

Figure 8:
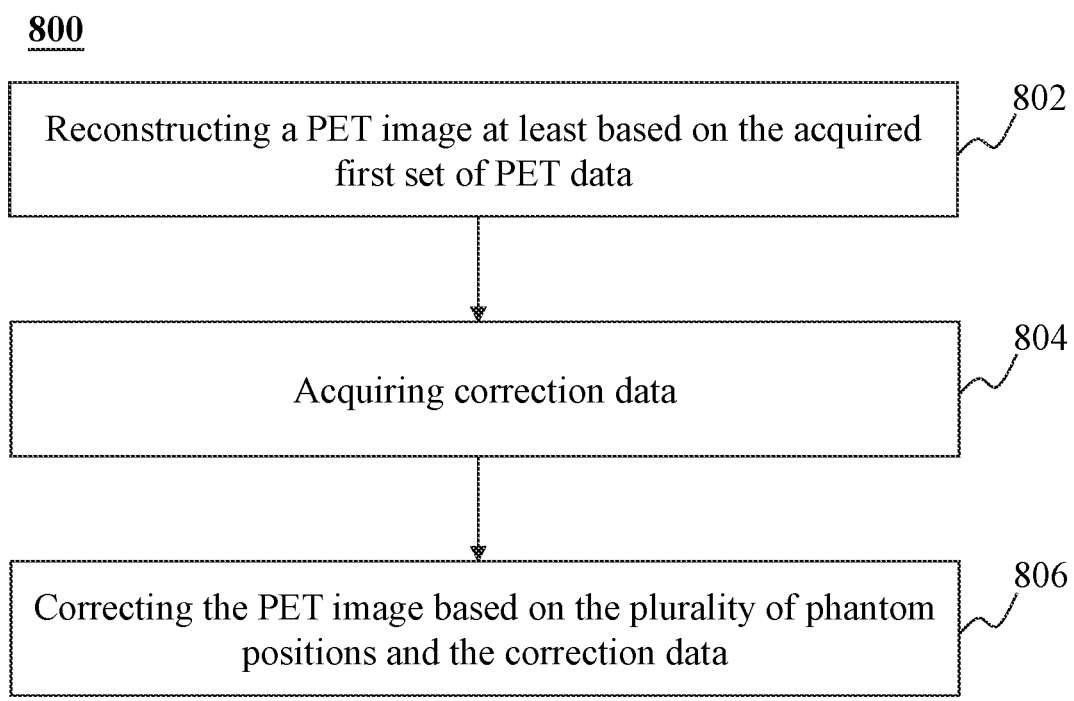
FIG. 8 is a flowchart illustrating an exemplary process for processing PET data according to some embodiments of the present disclosure.

FIG. 8 is a flowchart illustrating an exemplary process 800 for processing PET data according to some embodiments of the present disclosure.

In 802, the PET image reconstruction unit 241 may reconstruct a PET image at least based on the acquired first set of PET data. For example, the PET image reconstruction unit 241 may reconstruct the PET image based on the acquired first set of PET data and the plurality of phantom positions corresponding to the first set of PET data for the phantom. One or more reconstruction algorithms may be employed to reconstruct the PET image. Exemplary reconstruction algorithms may be illustrated elsewhere in the present disclosure.

In 804, the correction unit 242 may acquire correction data. For example, the correction unit 242 may acquire the first set of attenuation data for the phantom. As another example, the correction unit 242 may acquire the nuclide decay information for the phantom.

In 806, the correction unit 242 may correct the reconstructed PET image based on the plurality of phantom positions and the correction data. For example, the correction unit 242 may correct the reconstructed PET image based on the plurality of phantom positions and the nuclide decay information for the phantom. As another example, the correction unit 242 may correct the reconstructed PET image based on the first set of attenuation data for the phantom and the plurality of phantom positions.

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, a step in which the correction data may be stored may be added to the process 800.

Figure 9:
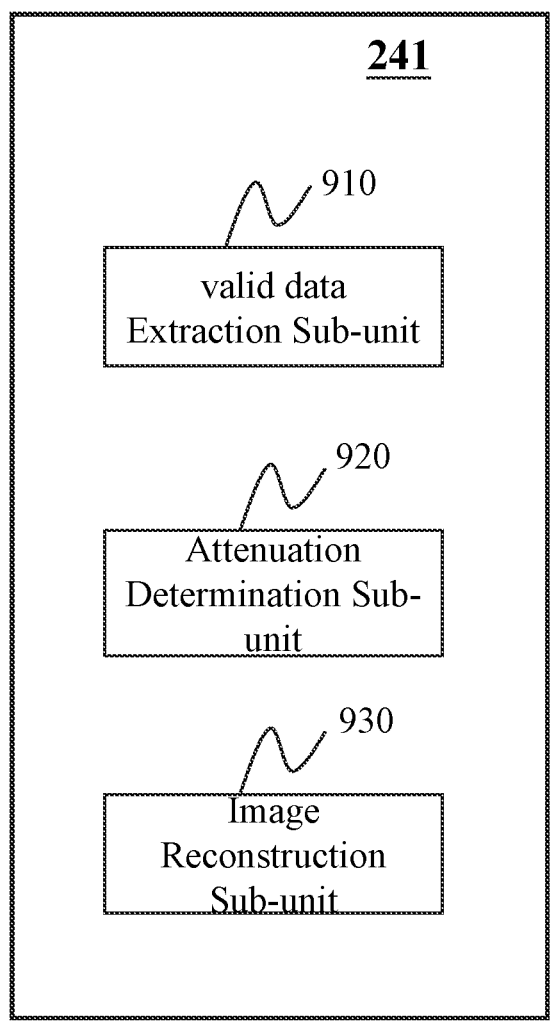
FIG. 9 is a block diagram illustrating an exemplary PET image reconstruction unit according to some embodiments of the present disclosure.

FIG. 9 is a block diagram illustrating an exemplary PET image reconstruction unit 241 according to some embodiments of the present disclosure. As illustrated, the PET image reconstruction unit 241 may include a valid data extraction sub-unit 910, an attenuation determination sub-unit 920, and an image reconstruction sub-unit 930.

The valid data extraction sub-unit 910 may extract the second set of PET data (or referred to as valid scanning data) from the first set of PET data. As described above, the first set of PET data may refer to original PET data collected by the detector units at the plurality of phantom positions (e.g., phantom position 1, phantom position 2, etc.). The original PET data may include valid scanning data corresponding to the phantom and invalid PET data not corresponding to the phantom. Merely by way of example, when the phantom is placed at a certain phantom position of the plurality phantom positions, scanning data corresponding to the phantom may be detected by a certain number of detector units of the detector 114 that are within a spatial range related to the phantom position. Meanwhile, one or more detector units beyond the spatial range may detect data not relating to the phantom (or referred to as invalid scanning data). The valid data extraction sub-unit 910 may extract the valid scanning data (or referred to as the second set of PET data) from the first set of PET data based on the corresponding phantom position. Merely by way of example, for each of at least one phantom position of the plurality of phantom positions, the valid data extraction sub-unit 910 may determine data collected by the detector units within a predetermined spatial range related to the phantom position to be valid scanning data and extract the determined valid scanning data from the first set of PET data. The extracted valid scanning data corresponding to the plurality of phantom positions may constitute the second set of PET data. In some embodiments, the valid data extraction sub-unit 910 may transmit the extracted second set of PET data to the image reconstruction sub-unit 930.

The attenuation determination sub-unit 920 may determine a second set of attenuation data for the phantom. As used herein, the second set of attenuation data for the phantom may to attenuation data corresponding to the entire FOV of the PET system 100. In some embodiments, the attenuation determination sub-unit 920 may determine the second set of attenuation data for the phantom based on the plurality of phantom positions and the first set of attenuation data which corresponds to part of the FOV of the PET system 100. In some embodiments, the attenuation determination sub-unit 920 may further employ a relationship between the phantom position and the attenuation data may to determine the second set of attenuation data for the phantom. In some embodiments, the attenuation determination sub-unit 920 may transmit the determined second set of attenuation data for the phantom to the image reconstruction sub-unit 930.

The image reconstruction sub-unit 930 may reconstruct a PET image based on the second set of PET data and the second set of attenuation data. For example, the image reconstruction sub-unit 930 may reconstruct the PET image based on the second set of PET data. As another example, the image reconstruction sub-unit 930 may reconstruct the PET image based on the second set of PET data and the second set of attenuation data for the phantom. The image reconstruction sub-unit 930 may employ an image reconstruction algorithm to reconstruct the PET image. Exemplary image reconstruction algorithms may be illustrated elsewhere in the present disclosure.

It should be noted that the above description of the PET image reconstruction unit 241 is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure. For example, the valid data extraction sub-unit 910 may be omitted and the function of the valid data extraction sub-unit 910 may be realized by the image reconstruction sub-unit 930.

FIG. 10 is a flowchart illustrating an exemplary process 1000 for processing PET data according to some embodiments of the present disclosure.

In 1002, the valid data extraction sub-unit 910 may extract a second set of PET data from first set of PET data based on a plurality of phantom positions of a phantom. The first set of PET data may be collected at the plurality of phantom positions. The second set of PET data may correspond to one or more coincidence events of the phantom. The valid data extraction sub-unit 910 may extract the second set of PET data from the first set of PET data based on the corresponding phantom position. Merely by way of example, for each of at least one phantom position of the plurality of phantom positions, the valid data extraction sub-unit 910 may extract a set of data collected by the detector units within a predetermined spatial range relating to the phantom position. The extracted plurality sets of data, which may correspond to the at least one phantom position of the plurality of phantom positions, may constitute the second set of PET data.

In 1004, the attenuation determination sub-unit 920 may acquire a first set of attenuation data for the phantom, the first set of attenuation data corresponding to part of FOV of an imaging device.

In 1006, the attenuation determination sub-unit 920 may determine a second set of attenuation data for the phantom corresponding to the FOV of the imaging device based on the plurality of phantom positions and the first set of attenuation data. For example, the second set of attenuation data for the phantom may correspond to the phantom position 1 and phantom position 2. The first set of attenuation data for the phantom may correspond to the phantom position 1. The attenuation determination sub-unit 920 may fill attenuation data for the phantom corresponding to the phantom position 2 based on the first set of attenuation data for the phantom, the phantom position 1 and the phantom position 2, which may further constitute the second set of attenuation data for the phantom with the first set of attenuation data for the phantom.

In 1008, the image reconstruction sub-unit 930 may reconstruct a PET image based on the second set of PET data and the second set of attenuation data. An image reconstruction algorithm may be employed to reconstruct the PET image. Exemplary image reconstruction algorithms may be illustrated elsewhere in the present disclosure.

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, operations 1004 and 1006 may be omitted, and the PET image may be reconstructed based on the second set of PET data.

FIG. 11 is a flowchart illustrating an exemplary process 1100 for correcting a PET image according to some embodiments of the present disclosure. The process may be executed by the correction unit 242.

In 1002, statistic data of phantom position may be generated by normalizing a plurality of phantom positions corresponding to FOV of an imaging device. A detector 114 of the imaging device may collect PET data related to the phantom while being placed at the plurality of phantom positions. While the phantom moves amongst the plurality of phantom positions, the phantom may accelerate or decelerate, thus introducing noise to the PET data collected by the detector 114. The correction unit 242 may normalize the plurality of phantom positions to reduce the introduced noise. A normalizing method may be employed to normalize the plurality of phantom positions.

In 1104, statistic data of nuclide decay may be generated by normalizing nuclide decay corresponding to the FOV. In some embodiments, the correction unit 242 may extract a plurality sets of nuclide decay information corresponding to the plurality of phantom positions corresponding to the FOV from the nuclide decay corresponding to the FOV, respectively. The extracted plurality sets of nuclide decay information may be normalized to determine the statistic data of nuclide decay. A normalizing method may be employed to normalize the plurality of phantom positions.

In 1106, the second set of PET data may be corrected based on the statistic data of phantom position and the statistic data of nuclide decay. Merely by way of example, the correction unit 242 may perform an axial count correction on the second set of PET data based on the statistic data of phantom position and statistic data of nuclide decay.

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. In operation 1104, the first set of PET data rather than the second set of PET data may be corrected based on the statistic data of phantom position and the statistic data of nuclide decay.

Figure 12:
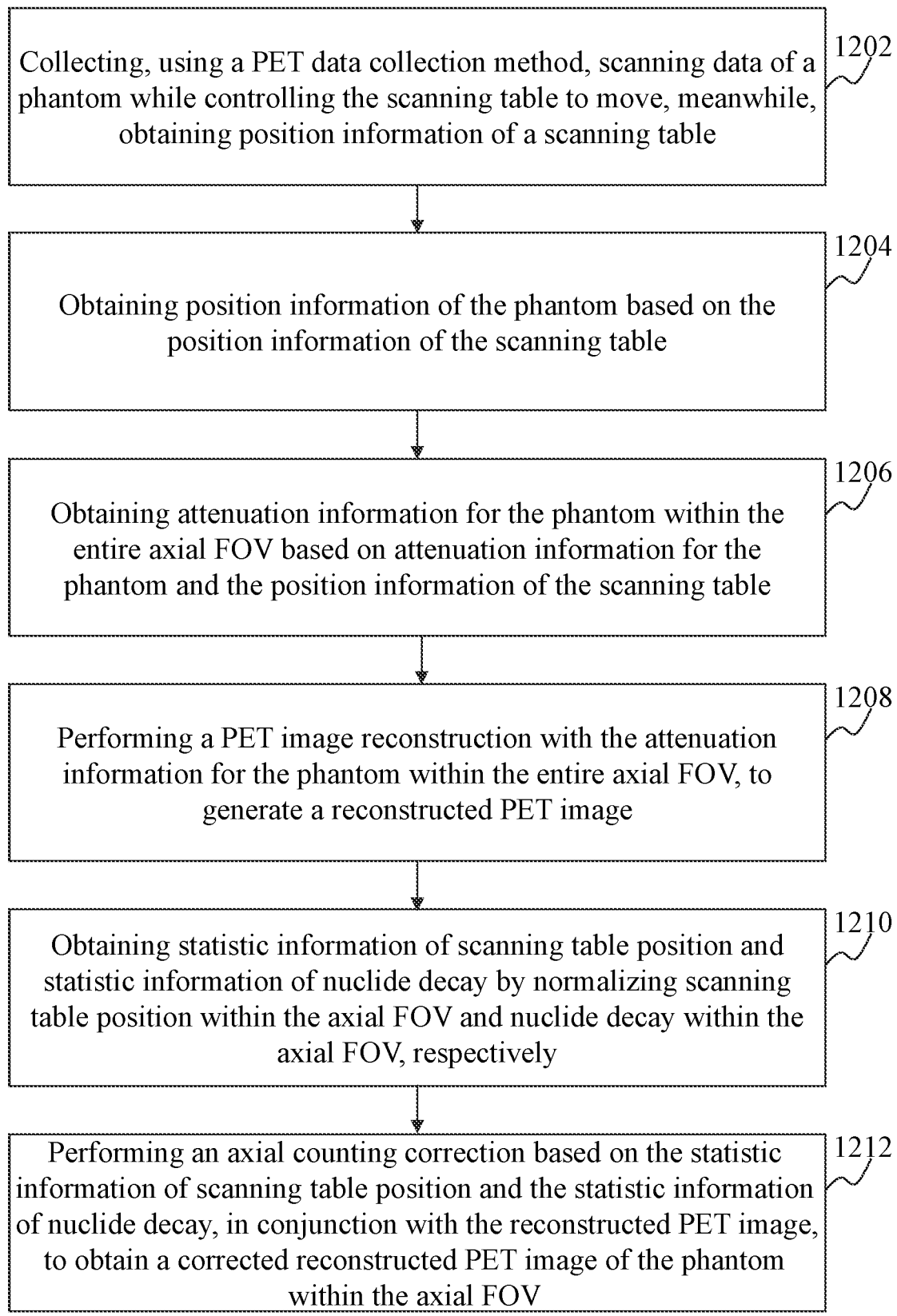
FIG. 12 is a flowchart illustrating an exemplary process for reconstructing a PET image according to an embodiment of the present disclosure.

The present disclosure also provides a method for reconstructing the PET image. FIG. 12 is a flowchart illustrating an exemplary process for reconstructing a PET image according to an embodiment of the present disclosure. As shown in FIG. 12, the method of reconstructing the PET image may include the following steps.

In 1202, scanning data of the phantom may be collected by using the PET data collection method described above. In some embodiments, in the process of collecting data of the phantom by the detector 114, a movement of the scanning table 112 may be controlled so that the predetermined detector units may be irradiated. The PET data collection method may be specified as described above and will not be described here. In some embodiments, the movement range of the phantom along the axis may correspond to an axial length larger than or equal to the length of the axis of FOV of the detector 114 so that all detector units may collect data of the phantom.

Position information of the scanning table 112 may be generated while the scanning table 112 is moved. Scanning data may be generated while the detector 114 is detecting coincidence events. The scanning data may include, for example, a plurality of coincidence events detected by the detector 114 and line of response (LOR)s corresponding to the plurality of coincidence events. As used herein, an LOR may refer to a line that connects the detector units that have detected two gamma photons of a coincidence event.

In some embodiments, the generated position information of the scanning table 112 and the scanning data related to the phantom may be further stored in a storage. In some embodiments, corresponding data may be read or retrieved from the storage during the subsequent PET image reconstruction.

In 1204, the position information of the phantom may be obtained based on the position information of the scanning table 112.

During the data collection process of the phantom, since the length of the axis of the phantom is shorter than the length of the axis of FOV of the detector 114, at a certain time point, some detector units may be able to collect the scanning data of the phantom while the other detector units, which may not be irradiated by the phantom, may collect scanning data that does not correspond to the phantom. The scanning data corresponding to the phantom may also be referred to as valid scanning data, and the scanning data not corresponding the phantom may also be referred to as invalid data. An image reconstruction should be based on the scanning data of the phantom (e.g., valid scanning data). Therefore, it may be necessary to extract valid scanning data corresponding to the phantom and discard invalid scanning data that does not correspond to the phantom to generate a more accurate PET image. In some embodiments, the valid scanning data corresponding to the phantom may be determined based on the position information of the scanning table 112 at the corresponding time point. In some embodiments, the position information of the phantom may be obtained based on the position information of the scanning table 112 to further extract the valid scanning data corresponding to the phantom.

In some embodiments, the corresponding scanning data may be extracted from the collected scanning data based on the position information of the phantom to perform the PET image reconstruction.

As described above, after obtaining the position information of the phantom, the valid scanning data corresponding to the phantom may be extracted. In some embodiments, the scanning data related to the phantom may be stored in the PET scan data unit 420, from which the corresponding scanning data may be extracted based on the position information of the phantom. In some embodiments, the corresponding scanning data may be determined based on the position information of the phantom and the length of the phantom.

Specifically, as shown in FIG. 12, the process of acquiring the valid scanning data corresponding to the phantom and perform the PET image reconstruction based thereon may include one or more of the following operations.

In step 1206, attenuation information for the phantom within the entire axial FOV may be obtained based on attenuation information for the phantom and the position information of the scanning table 112. The attenuation information for the phantom may be acquired, for example, by CT scanning. For example, CT scanning data of the phantom may be acquired by the CT scanning, based on which an attenuation map, or attenuation information for the phantom may be acquired.

As described above, in some embodiments, the length of the axis of the phantom may be shorter than the length of the axis of FOV of the detector 114, and the attenuation information for the phantom within the entire axial FOV may not be acquired during the CT scanning of the phantom, which may be performed to acquire the attenuation information for the phantom. Thus, in some embodiments according to the present disclosure, the position information of the scanning table 112 and the known attenuation information for the phantom (e.g., attenuation information corresponding to part of the axis of FOV of the detector 114) may be combined to fill the corresponding position in the axial scanning area with the corresponding attenuation information for the phantom, to acquire the attenuation information for the phantom within the entire axial FOV.

In 1208, a PET image reconstruction may be performed with the attenuation information for the phantom within the entire axial FOV, to generate a reconstructed PET image within the entire axial FOV.

In some embodiments, during the PET image reconstruction process, the valid scanning data may be extracted based on the position information of the phantom. Further, a PET image may be reconstructed based on the attenuation information for the phantom and the corresponding scanning data (e.g., the extracted valid scanning data).

The PET image reconstruction method may include, for example, a filtered back projection (FBP) or an ordered subset expectation-maximization (OSEM).

It should be noted that the recited order of the operations in FIG. 12 is not intended to limit the claimed process. For example, the sequence of the step in which the information for the phantom and the step in which the valid scanning data may be extracted may be exchanged, with a premise that the attenuation information for the phantom and the valid scanning data are available at the time of performing the PET image reconstruction.

In some embodiments, the method of reconstructing the PET image further may include the following steps:

In step 1210, the statistic information of scanning table position and the statistic information of the nuclide decay may be obtained by normalizing the scanning table positions within the axial FOV and the nuclide decay within the axial FOV of the detector 114, respectively.

The statistic information of the scanning table position may be obtained by extracting and normalizing the position information of the scanning table 112 and the position or length information of the phantom stored in the PET scan data unit 420. During the data collection process, the movement of the scanning table 112 may drive the phantom to move. In some embodiments, when the scanning table 112 moves, the scanning table 112 may accelerate or decelerate, which may drive the phantom to accelerate or decelerate accordingly. In some embodiments, thorough normalizing the corresponding position information of the scanning table 112, the position of the phantom (the position information of the phantom on the scanning table 112) and/or the length of the phantom at each time point, image differences that may be generated due to the acceleration or deceleration of the scanning table 112 and other factors during the movement of the scanning table 112 may be corrected to reconstruct a more accurate PET image.

Similarly, the statistic information of the nuclide decay may also be obtained by extracting nuclide decay information at the corresponding time point from the PET scan data unit 420 based on the position information of the scanning table 112 and by normalizing the nuclide decay within the axial FOV of the detector 114. That is, due to the radioactive decay of the nuclide, the nuclide decay information extracted based on the position information of the scanning table 112 at each time point may be normalized, to avoid a deviation that the reconstructed image may have due to the nuclide decay.

In 1212, an axial count correction may be performed based on the statistic information of the scanning table position and the statistic information of the nuclide decay within the axial FOV, and the reconstructed PET image, to obtain a corrected PET image of the phantom within the entire axial FOV.

After operation 1208, in which the reconstructed PET image may be obtained, the reconstructed PET image may be axially corrected by further combining the statistic information of the scanning table position and the statistic information of the nuclide decay within the axial FOV to eliminate the image differences due to the acceleration, deceleration of the scanning table 112 and other factors, and further to avoid the impact of the nuclide decay on the reconstructed image. Thus, a more accurate corrected reconstructed PET image of the phantom within the entire axial FOV may be obtained. In this way, the reconstructed PET image may be analyzed to further obtain the performance and working condition of the PET system 100. For example, the axial uniformity of the PET system 100 may be verified based on the reconstructed PET image.

In some embodiments, the PET image may be reconstructed by using the data of the phantom collected by all detector units, so that the quality analysis may be performed based on the generated reconstructed PET image. In other embodiments, the normalizing factor of the detector efficiency may be generated by using the data of the phantom obtained by the PET data collection method described above.

In some embodiments, there may be tens of thousands of detector units in the detector 114 of the PET system 100. The detection efficiency of the detector units may be inconsistent due to their respective geometric positions and performance differences. The performance differences of the detector units may be due to factors including different luminous efficiencies of crystal strips of the detector units, different coupling extents between the crystal strips and photomultiplier tubes in the detector units, and different angles of the crystal strips with respect to coincidence lines. The inconsistency of the detection efficiency of the detector units may introduce artifacts in the PET image reconstruction. Therefore, to accurately model the detector units and to obtain a satisfactory image quality, the detection efficiencies of the detector units of the detector 114 may be normalized. The normalization of the detection efficiencies may also be referred to as a normalizing calibration. The normalizing calibration method of the detector efficiency may be illustrated elsewhere in the present disclosure. In some embodiments, the normalizing calibration method of the detector efficiencies may include a plurality of factors (e.g., a plurality of normalizing factors), which may be stored in a computer in a file format. In some embodiments, while a patient is scanned by the PET system 100, the normalizing factor may be applied to a measured value of the detector 114 to perform the normalizing calibration of the detector efficiency.

Figure 13:
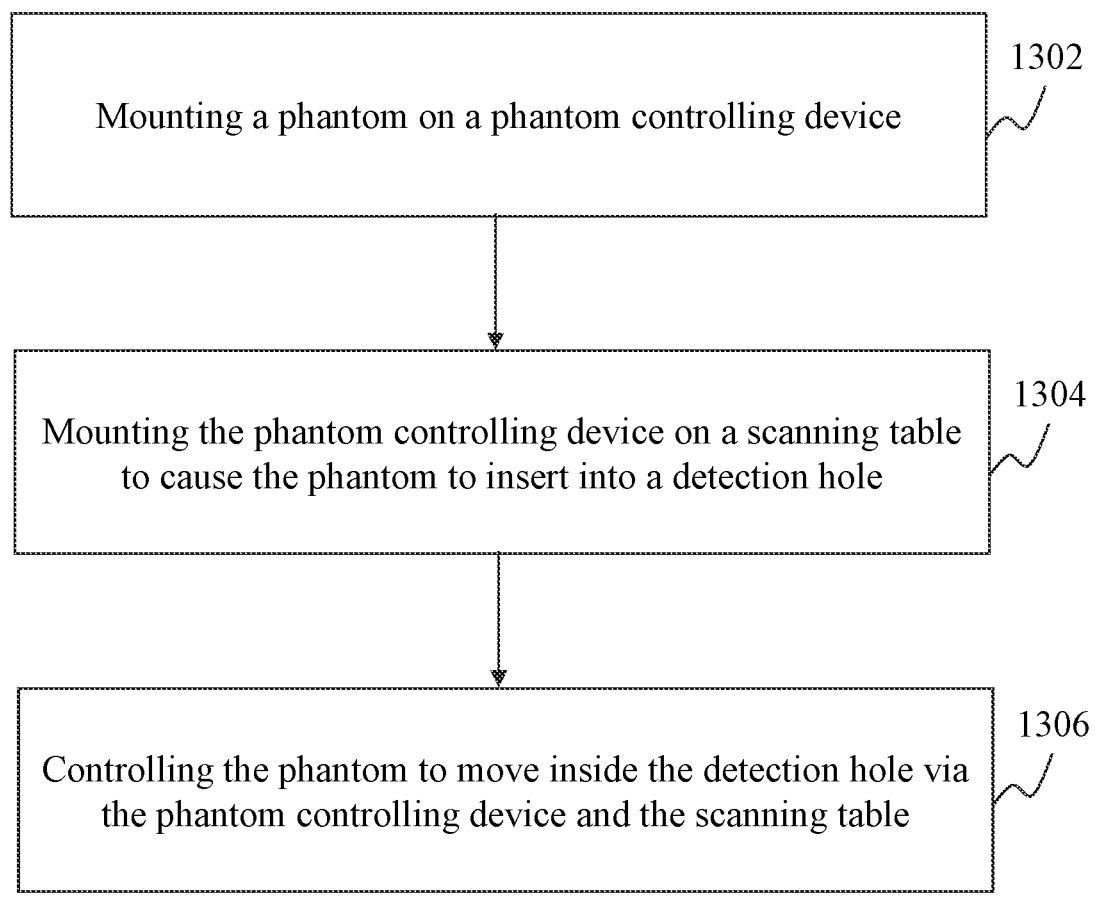
FIG. 13 is a flowchart illustrating an exemplary process for controlling a phantom of a medical imaging device with a first motion controller according to an embodiment of the present disclosure.

FIG. 13 is a flowchart illustrating an exemplary process for controlling a phantom of a medical imaging device with a first motion controller according to an embodiment of the present disclosure. Refer to FIG. 13, in 1302, a phantom may be mounted on a phantom controlling device (or referred to as the second moving mechanism). In 1304, the phantom controlling device may be mounted on the scanning table 112 to cause the phantom to insert into the detection region 113. In 1306, the phantom may be controlled to move inside the detection region 113 via the phantom controlling device and the scanning table 112. In some embodiments, the phantom controlling device may include a moving mechanism that may drive the phantom to move along the X direction inside the detection region 113. In some embodiments, the scanning table 112 may include a scanning-table driving mechanism (or referred to as the first moving mechanism) that may drive the scanning table 112 to move along a forward-backward (e.g., the Y direction shown in FIG. 1) and/or an up-down direction (e.g., the Z direction shown in FIG. 1). The moving mechanism may move along the he Y direction and/or the Z direction inside the detection region 113 based on the effect of the scanning-table driving mechanism. In other embodiments, the phantom may be controlled to move circumferentially inside the detection region 113 via the phantom controlling device and the scanning table 112.

Figure 14:
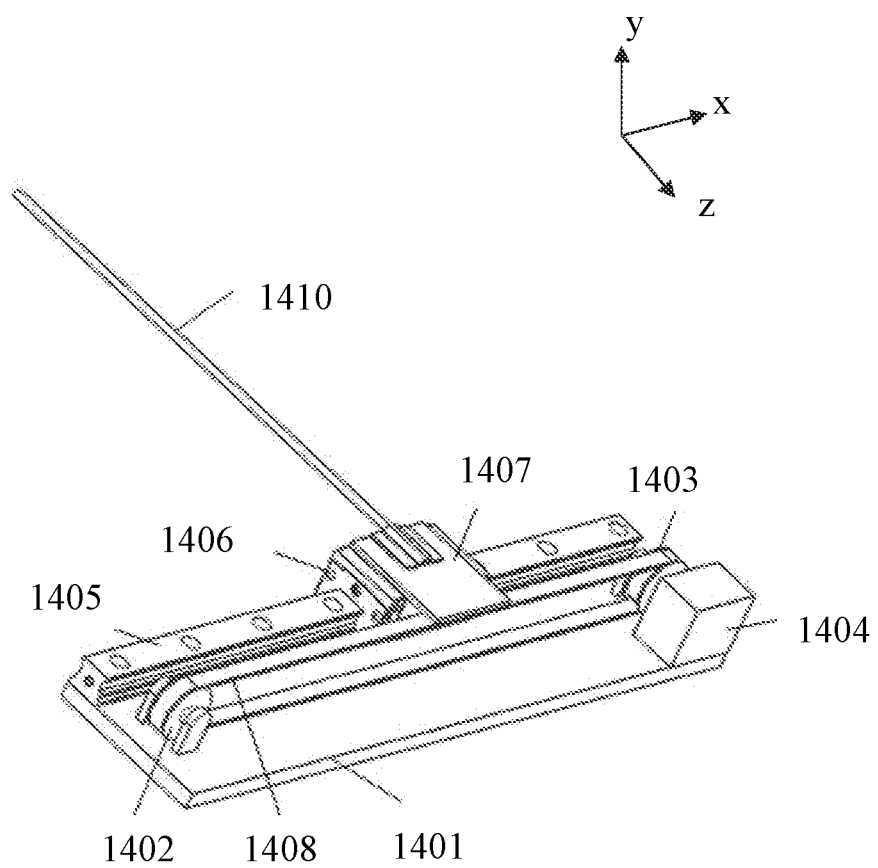
FIG. 14 is a schematic diagram illustrating a phantom controlling device according to an embodiment of the present disclosure.

FIG. 14 is a schematic diagram illustrating a phantom controlling device (or referred to as the first phantom controlling device, or the second moving mechanism) according to an embodiment of the present disclosure. Referring to FIG. 14, the phantom controlling device may include a phantom bearing 1407 and a moving mechanism. The moving mechanism may include a support plate 1401, a first rotation wheel 1402 and a second rotation wheel 1403 which are installed at both ends of the support plate 1401, a transmission belt 1408 sheathed on the first rotation wheel 1402, and the second rotation wheel 1403. The transmission belt 1408 may extend along the X direction. The phantom 1410 may be connected to the transmission belt 1408 via the phantom bearing 1407, and the first rotation wheel 1402 and/or the second rotation wheel 1403 may be connected to a driver 1404 (e.g., a first driver). When the driver 1404 is started, the first rotation wheel 1402 and the second rotation wheel 1403 may drive the transmission belt 1408 to move along the X direction and the phantom 1410 may be moved with the transmission belt 1408 along the direction. The phantom 1410 may be driven to reciprocate along the direction. In one embodiment, the first rotation wheel 1402 and the second rotation wheel 1403 may be mounted on the support plate 1401 via a supporting frame, and the transmission belt 1408 and the first rotation wheel 1402 and the second rotation wheel 1403 may be gear-driven. In another embodiment, the moving mechanism may include a guide structure, and the phantom 1410 may be connected to the guide structure via the phantom bearing 1407 (e.g., a connecting plate) and may move along the guide structure. In a specific embodiment, the guide structure may be a guiding mechanism 1405 installed on the support plate 1401, and the guiding mechanism 1405 may be installed on one side of the transmission belt 1408 and may extend along the X direction. The guiding mechanism 1405 may be installed with a slider block 1406. The phantom 1410 may be mounted on the connecting plate 1407. One end of the connecting plate 1407 may be connected to the slider block 1406 and the other end thereof may be connected to the transmission belt 1408. The phantom 1410 may move along the guiding mechanism 1405, along with the transmission belt 1408.

FIG. 15 is a schematic diagrams illustrating a phantom controlling device (or referred to as a first phantom controlling device, or the second moving mechanism) according to another embodiment of the present disclosure. Referring to FIG. 15, the phantom controlling device may include a phantom bearing 1507 (e.g., a connecting plate) and a moving mechanism. The moving mechanism may include a support plate 1501 and a screw shaft 1502 installed on the support plate 1501. The screw shaft 1502 may extend along the X direction (e.g., a direction perpendicular to the axial direction of the detection region 113). The phantom 1510 may be mounted on a support base 1503 via the phantom bearing 1507, the support base 1503 may be sheathed on the screw shaft 1502, and the end of the screw shaft 1502 may be connected to a driver 1504 (or referred to as a second driver). When the driver 1504 is started, the screw shaft 1502 may drive the support base 1503 and the phantom 1510 to reciprocate along the X direction. In one embodiment, the screw shaft 1502 may be mounted on the support plate 1501 via the supporting frame. In another embodiment, the moving mechanism may include a guide structure, and the phantom 1510 may be connected to the guide structure via the phantom bearing 1507 and may move along the guide structure. In a specific embodiment, the guide structure may be a guiding mechanism 1505 installed on the support plate 1501. The guiding mechanism 1505 may be installed on one side of the screw shaft 1502 and may extend along the X direction. A slider block 1506 may be installed on the guiding mechanism 1505. The phantom 1510 may be mounted on the connecting plate 1507. One end of the connecting plate 1507 may be connected to the slider block 1506, while the other end thereof may be connected to the support base 1503. The phantom 1510 may move along the guiding mechanism 1505 with the rotation of the screw shaft 1502. In some embodiments, the guiding mechanism 1505 may be installed beneath the screw shaft 1502 and the support base 1503 may be mounted on the guiding mechanism 1505. A groove may be installed on the surface of the support base 1503 facing the guiding mechanism 1505, so that the support base 1503 may slide along the guiding mechanism 1505.

The moving mechanism may drive the phantom 1510 to move along the X direction inside the detection region 113. The movement may be of a uniform or non-uniform velocity, may be a continuous movement within a certain period of time, or may be a discontinuous movement separated by at least one time interval. The present disclosure is not intended to limit the scope of the mode in which the moving mechanism may drive the phantom 1510 to move along the X direction inside the detection region 113.

Figure 16:
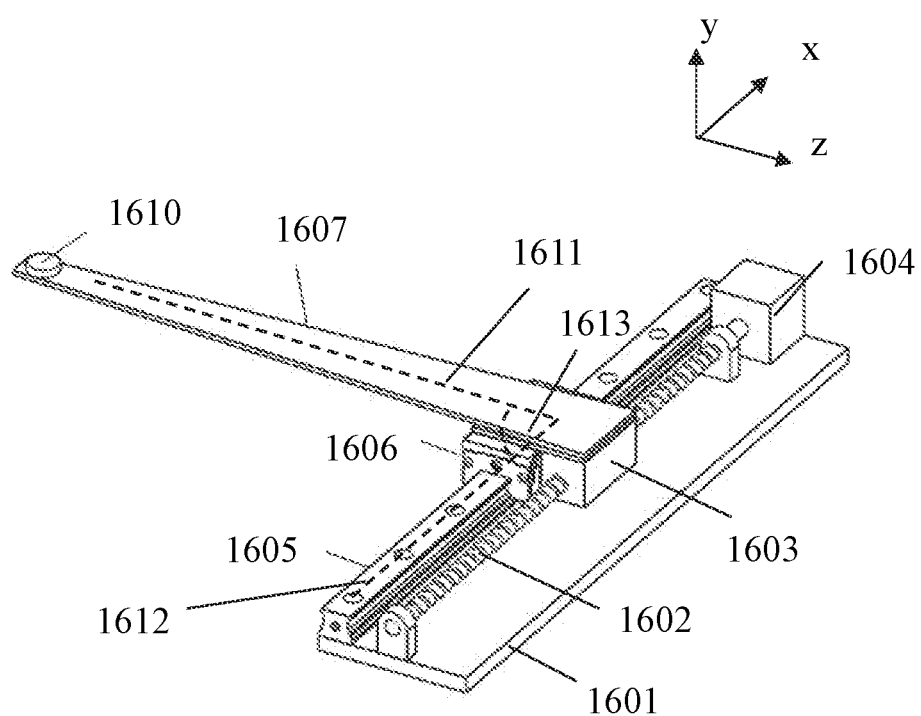
FIG. 16 is a schematic diagram illustrating a phantom controlling device according to another embodiment of the present disclosure.

FIG. 16 is a schematic diagrams illustrating a phantom controlling device according to another embodiment of the present disclosure. As illustrated, the phantom controlling device may include a support plate 1601, screw shaft 1602, support base 1603, driver 1604, guiding mechanism 1605, slider block 1606 and a connecting plate 1607. The function of the phantom controlling device may be illustrated in FIG. 14 and/or FIG. 15. The configuration of the connecting plate 1607 and the manner in which the phantom 1610 is located in the connecting plate 1607 may be different with respect to those illustrated in FIG. 14 and/or FIG. 15.

The phantom 1610 may be a point phantom, a line phantom, a rod phantom, etc. As shown in FIGS. 14 and 15, the phantom may be a rod phantom. As shown in FIG. 16, the phantom 1610 may be a point phantom and the point phantom 1610 may be installed at an end of a connecting plate 1607. In one embodiment of the disclosure, the angle 1613 between the extension direction of the phantom on the connecting plate 1611 and the extension direction of the moving mechanism 1612 may be any angle greater than zero, such as 10 degrees, 20 degrees, 30 degrees or 90 degrees. In another embodiment, the phantom 1610 and the connecting plate 1607 may be detachably connected to facilitate the installment or replacement of the phantom 1610. In other embodiments, the phantom 1610 (e.g., a rod phantom) or the connecting plate 1607 may be connected to a rotation mechanism (not shown). When the phantom is required for scanning, the rotation mechanism may be operated so that the angle 1613 between the extension direction of the phantom 1611 and the extension direction of the moving mechanism 1612 may be greater than zero. When the phantom is not required, the phantom may be rotated so that the extension direction of the phantom may be the same as that of the moving mechanism, so that the phantom and the moving mechanism may be accommodated in the shield cover for storage.

The motion control of the phantom in the Y1 direction as shown in FIG. 1 or FIG. 16 may be achieved by the above-described phantom controlling device. The phantom controlling device may be placed on the scanning table 112. In some embodiments, the phantom controlling device may be placed on the top surface of the scanning table 112 near a frame (e.g., the gantry 111 of the PET system 100). The support plate 1601 may be inserted directly into a head support socket of the scanning table 112 to be fixed onto it. The phantom 1610 mounted on the phantom controlling device may be inserted into the detection region 113 by adjusting the position of the scanning table 112. The phantom controlling device may drive the phantom 1610 to move along the X direction (e.g., a direction perpendicular to the axial direction of the detection region 113) inside the detection region 113. The position of the phantom 1610 in a direction perpendicular to the Z direction of the detection region 113 may also be adjusted to meet the requirements for precise positioning of the phantom 1610. The driver may also be adjusted to meet the requirements to achieve a certain motion trail of the phantom 1610. For example, in the PET resolution test, the above-described phantom controlling device may position the phantom 1610 at different positions to meet the requirements for precise positioning of the phantom 1610. In addition, the phantom controlling device may drive a rod phantom 1610 to move along the X direction to simulate a plane phantom.

In some embodiments of the present disclosure, the scanning table 112 may include a scanning table driving mechanism that may drive the scanning table 112 to move along the Z direction and/or the Y direction. The scanning table driving mechanism may drive the moving mechanism to move inside the detection region 113. The movement of the moving mechanism may be of a uniform or non-uniform velocity, may be a continuous movement within a certain period of time, or may be a discontinuous movement separated by at least one time interval. The present disclosure is not intended to limit the scope of the mode in which the scanning table moving mechanism drive the moving mechanism.

The phantom may move in a certain direction, or in a certain plane while driven by the phantom controlling device and/or the scanning table 112. For example, the phantom controlling device (or the scanning table 112) may drive the phantom to move along the X direction or the Y direction. As another example, the scanning table 112 may drive the phantom controlling device to move along the Y direction and/or the Z direction. As another example, the phantom controlling device may drive the phantom to move in the X direction, while the scanning table 112 may drive the phantom to move in the Y direction, resulting in a movement in the X-Y plane of the phantom. The movement trail of the phantom may be regular or irregular in shape. For example, the movement trail of the phantom may be circular.

Figure 17:
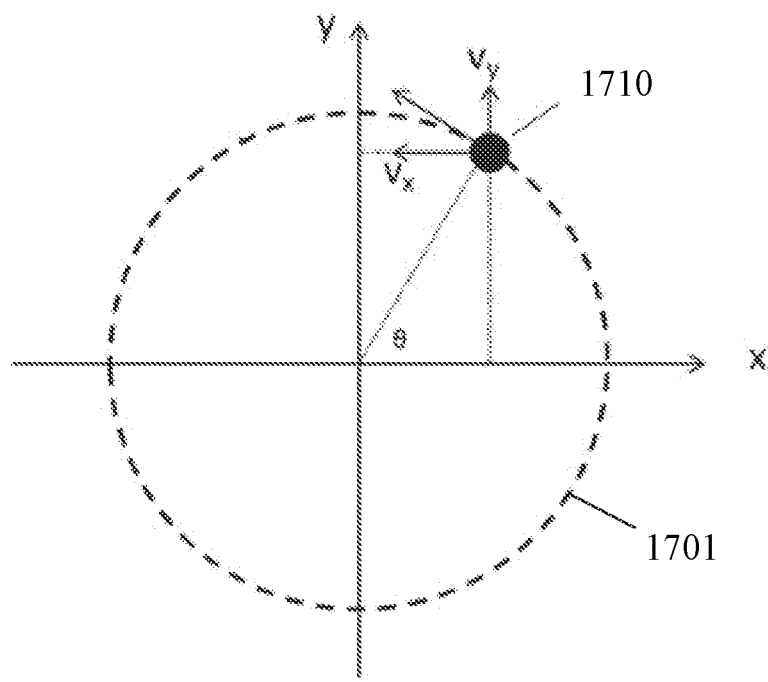
FIG. 17 is a schematic diagram illustrating a circular motion according to some embodiments of the present disclosure.

FIG. 17 is a schematic diagram illustrating a circular movement trail of the phantom according to some embodiments of the present disclosure.

Referring to FIG. 17, the phantom 1710 may move in a circular trail 1701 on the X-Y plane, around the Z axis. The phantom 1710 may move in a circular trail 1701 at a uniform velocity when the equation (2) to equation (5) are satisfied:

$$v_x = v \times \sin\theta = rw\sin(wt), \quad (2)$$

$$v_y = v \times \cos\theta = rw\cos(wt), \quad (3)$$

$$v = rw, \quad (4)$$

$$\theta = wt, \quad (5)$$

wherein v denotes the uniform velocity of the phantom 1710, and w denotes an angular velocity of the phantom 1710, and θ denotes an angle between the axis of the phantom 1710 and the Z direction. Vx denotes a velocity of the phantom in the X direction. The phantom 1710 may be driven by the moving mechanism. Vy denotes a velocity of the phantom in the Y direction. In some embodiments, a vertical lifting mechanism in the scanning table 112 may be utilized to drive the phantom 1710 to move in the Y direction.

The movement of the scanning table 112 and the phantom 1710 controlling device may be of a uniform or non-uniform velocity. In some embodiments, to obtain a circular movement of the phantom 1710, the speed of the phantom 1710 may be precisely controlled to be uniform during its movement. In some embodiments, the scanning table driving mechanism and/or the phantom controlling device may communicate with a computer to control the movement of the phantom 1710 together. The scanning table driving mechanism and/or the phantom controlling device may drive the phantom 1710 to move under an instruction sent out by the computer. In some embodiments, a movement trail may be input into the computer based on which one or more instructions may be generated. The computer may further send the generated instructions to the phantom controlling device and/or the scanning table driving mechanism to control the phantom 1710 to move in the movement trail that has been input to the computer.

Figure 18A:
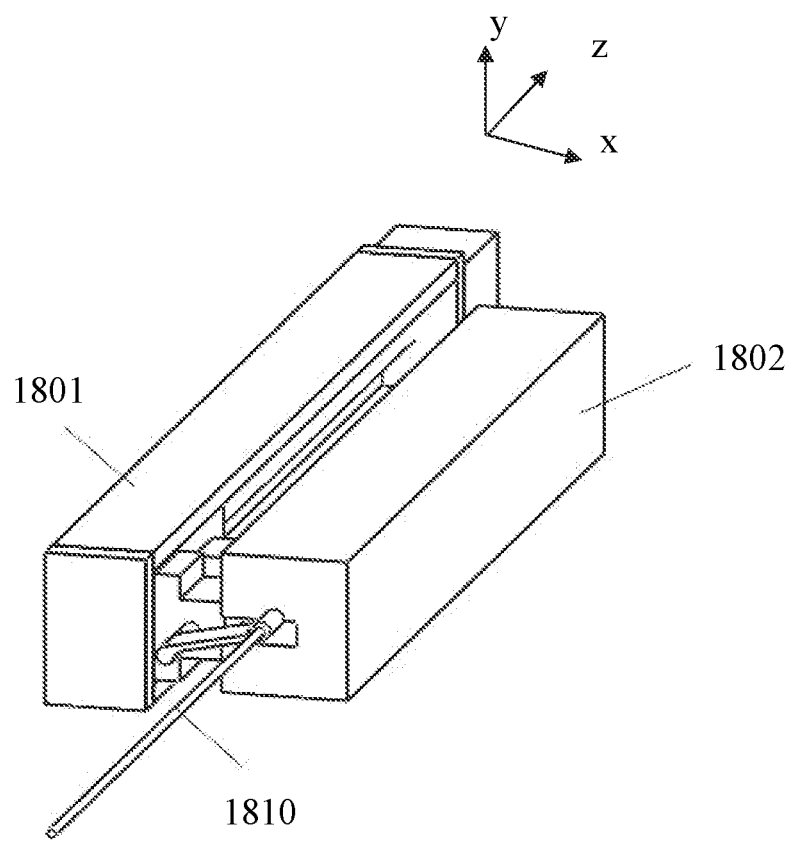
FIG. 18A is a schematic diagram illustrating a phantom controlling device according to an embodiment of the present disclosure.

FIG. 18A is a schematic diagram illustrating a phantom controlling device (or referred to as a second phantom controlling device, or the second motion controller) according to some embodiments of the present disclosure. As shown in FIG. 18A, the phantom controlling device may include a first shield 1801, a second shield 1802 and a phantom 1810. The phantom 1810 (e.g., a point phantom, a line phantom, a rod phantom, etc.) may be installed in a radiation shielding space formed by the first shield 1801 and the second shield 1802 and may stretch out or retract into the second shield 1802. When a subject (e.g., a human body) is scanned by the PET system 100, the phantom 1810 may retract into the second shield 1802 to prevent the subject from being affected by the radiation from the phantom 1810. When the PET system 100 is to be tested or calibrated, as shown in FIG. 1, radiations of the phantom may be required to accomplish the test or calibration. Thus, the phantom 1810 may stretch out from the second shield 1802 and extend into the detection region 113 to radiate the detectors of the PET system.

The phantom controlling device may be mounted beneath the scanning table. For example, the phantom controlling device may be mounted on the bottom surface of the scanning table 112 that is close to the gantry 111.

Figure 18B:
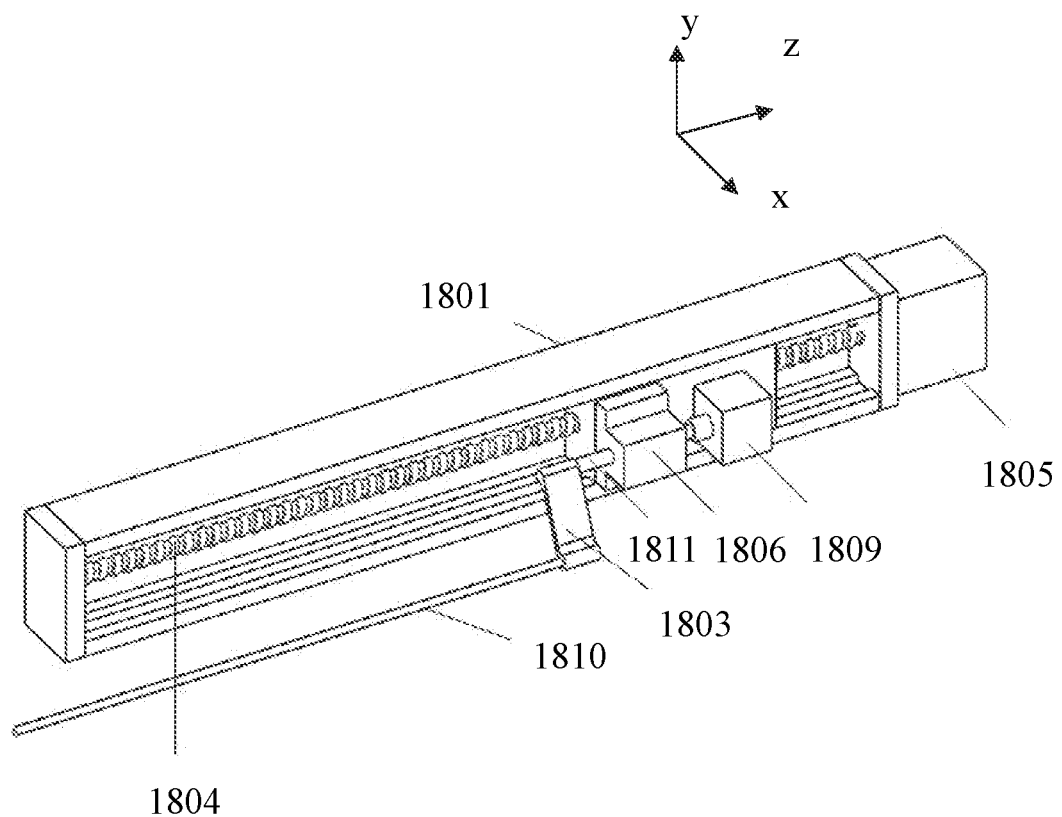
FIG. 18B is a schematic diagram illustrating an internal structure of a first shield according to an embodiment of the present disclosure.

FIG. 18B is a schematic diagram illustrating an internal structure of a first shield 1801 according to some embodiments of the present disclosure. As shown in FIG. 18B, the first shield 1801 has a first groove extending along the Z direction. A screw shaft 1804 may be installed in the groove. The phantom 1810 may be installed on a slider block 1806 that is sheathed on the crew shaft 1804. One end of the crew shaft 1804 may be connected to a first motor 1805, and the first motor 1805 may be installed at one end of the first shield 1801. The first motor 1805 may drive the crew shaft 1804 to drive the phantom 1810 to move via the slider block 1806. In some embodiments of the present disclosure, a guide structure (e.g., a guide trail) may be mounted on at least one surface of the first groove, along which the slider block 1806 may slide. The phantom controlling device may further comprise a phantom driving device. The phantom driving device may include a rotation shaft 1811 and a rotation arm 1803. One end of the rotation shaft 1811 may connect to a second motor 1809. The second motor 1809 may be installed on the slider block 1806, and may slide along the screw shaft 1804 with the slider block 1806. For example, the second motor 1809 may locate between the first shield 1801 and the second shield 1802. The phantom 1810 may be connected to the rotation arm 1803. The second motor 1809 may drive the rotation shaft 1811 to drive the phantom 1810 to rotate via the rotation arm 1803. In some embodiments of the disclosure, the rotation arm 1803 may be in a crank structure.

Figure 18C:
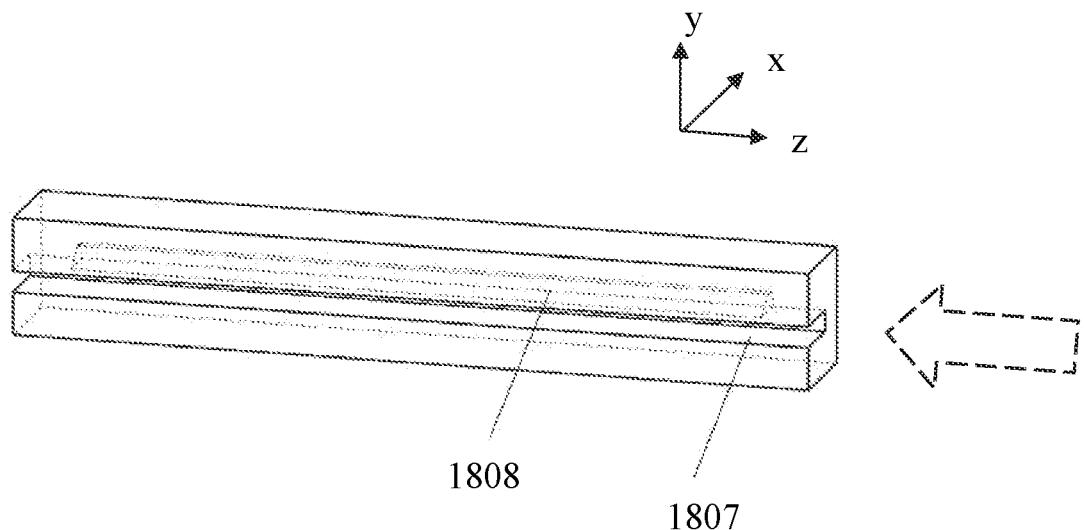
FIG. 18C is a schematic diagram illustrating the second shield according to an embodiment of the present disclosure.
Figure 18D:
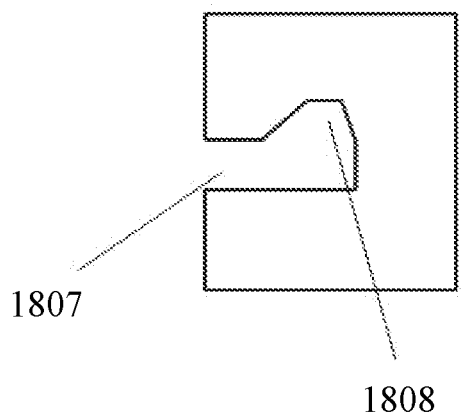
FIG. 18D is a cross-sectional view illustrating the second shield according to an embodiment of the present disclosure.

FIG. 18C is a schematic diagram illustrating a second shield according to some embodiments of the present disclosure. FIG. 18D is a cross-sectional view of the second shield according to some embodiments of the present disclosure. As shown in FIGS. 18C and 18D, the second shield 1802 may have, on its surface facing the phantom 1810, a second groove 1807 that extends along the Z direction. The end of the second groove, which faces the Y-Z plane, may include an opening. The second groove 1807 may provide the phantom 1810 with a moving passage. The motor 1805 may drive the phantom 1810 to stretch out or retract into the second shield 1802 through the second groove 1807. A third groove 1808, which may be configured to accommodate the phantom 1810, may locate on a surface of the second groove 1807. In some embodiments of the present disclosure, the third groove 1808 and the second groove 1807 may be on different planes. The third groove may include two closed ends. The two ends of the third groove may be along the Z direction. The phantom 1810 may retract into the second shield 1802 and may be accommodated in the third groove 1808, while the human body is scanned by the PET system 100.

To calibrate the PET system 100 with the phantom 1810, the first motor 1805 may drive the phantom 1810 to stretch out from the second shield 1802 to extend into the detection region 113. The second motor 1809 may drive the phantom 1810 to rotate at a uniform velocity inside the detection region 113 to irradiate the detector units within the detecting region 113. When the calibration of the PET system is finished, the first motor 1805 may drive the phantom 1810 to retract into the second shield 1802. The second motor 1809 may drive the phantom 1810 to enter a space formed by the third groove 1808 in the second shield 1802. The space may shied radiation emitted by the phantom 1810. In some embodiments, the phantom controlling device may further include a fixing device for fixing the phantom controlling device on the bottom surface of the scanning table 112. The fixing device may include a buckle, a nut, or the like, or any combination thereof.

In some embodiments, the scanning table 112 may further include a lifting device, through which the height of the scanning table 112 may be adjusted. When the PET device is calibrated using the phantom, the height of the scanning table 112 may be adjusted to coincide the axis of the rotation shaft 1811 and the axis of the ring of the FOV.

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the phantom controlling device may not only be used to calibrate a single modality imaging system such as the PET system 100 as illustrated, a Computed Tomography (CT) system, a MR (Magnetic Resonance) system, or the like, but may also be used to calibrate a multi-modality imaging system such as PET-CT device, PET-MR device, etc.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for medical imaging, comprising:
 a bed configured to support a phantom;
 a scanner configured to detect coincidence events related to the phantom; and
 a motion controller configured to move the phantom along an axis of the scanner to a plurality of phantom positions;

wherein the motion controller comprises a first motion controller, the first motion controller comprising:
  a first moving mechanism configured to move the bed in a first direction or a second direction; and
  a second moving mechanism configured to move the phantom in a third direction, the third direction is perpendicular to the first direction and the second direction.

2. The system of claim 1, wherein the motion controller is further configured to move the bed to drive the phantom to the plurality of phantom positions.

3. The system of claim 1, wherein the plurality of phantom positions are determined based on a scanning parameter of the scanner and a parameter of the phantom.

4. The system of claim 1, wherein the second moving mechanism comprises:
  a support plate;
  a first rotating wheel and a second rotating wheel disposed at two ends of the support plate;
  a first driver connected to the first rotating wheel and the second rotating wheel; and
  a transmission belt that encompasses the first rotating wheel and the second rotating wheel, wherein the transmission belt extends in the third direction, and is connected to the phantom.

5. The system of claim 1, wherein the second moving mechanism comprises:
  a support plate;
  a screw shaft disposed on the support plate, wherein the screw shaft extends in the third direction;
  a second driver connected to an end of the screw shaft; and
  a support base attached to the screw shaft, wherein the support base is connected to the phantom.

6. The system of claim 1, wherein the second moving mechanism comprises a guiding mechanism configured to guide the phantom to move.

7. The system of claim 6, wherein the phantom is connected to and moves along the guiding mechanism.

8. The system of claim 1, wherein the second moving mechanism comprises a shield configured to shield radiation from the phantom.

9. The system of claim 1, wherein the motion controller further comprises a second motion controller, and the second motion controller comprises a third moving mechanism comprising:
  a screw shaft extending along the first direction, wherein an end of the screw shaft is connected to a first driver;
  a slider block attached to the screw shaft, wherein the slider block is connected to the phantom; and
  a shield configured to accommodate the screw shaft, the slider block and the phantom.

10. The system of claim 9, wherein the second motion controller further comprises:
  a rotation shaft;
  a second driver mounted on the slider block, wherein the second driver is connected to an end of the rotation shaft; and
  a rotation arm configured to rotate the phantom under a force supplied by the rotation shaft.

11. The system of claim 9, wherein the shield comprises a first shield comprising a first groove, wherein the first groove extends along the first direction, and the screw shaft is disposed inside the first groove.

12. The system of claim 11, wherein the first groove comprises a guiding mechanism, and the slider block is configured to move along the guiding mechanism.

13. The system of claim 11, wherein the shield further comprises a second shield, a surface of the second field facing the phantom comprising a second groove configured to provide a moving passage for the phantom, wherein the second groove extends in the first direction.

14. The system of claim 13, wherein the second shield further comprises a third groove configured to accommodate the phantom, wherein the third groove is on a different plane from the second groove, and extends in the first direction.

15. The system of claim 14, wherein the third groove comprises two closed ends.

16. A system for medical imaging, comprising:
  a bed configured to support a phantom;
  a scanner configured to detect coincidence events related to the phantom; and
  a motion controller configured to move the phantom along an axis of the scanner to a plurality of phantom positions;
  wherein the motion controller comprises a second motion controller, and the second motion controller comprises a moving mechanism configured to move the phantom and accommodate the phantom.

17. The system of claim 16, wherein the moving mechanism comprises:
  a screw shaft extending along the first direction, wherein an end of the screw shaft is connected to a first driver;
  a slider block attached to the screw shaft, wherein the slider block is connected to the phantom; and
  a shield configured to accommodate the screw shaft, the slider block and the phantom.

18. The system of claim 17, wherein the second motion controller further comprises:
  a rotation shaft;
  a second driver mounted on the slider block, wherein the second driver is connected to an end of the rotation shaft; and
  a rotation arm configured to rotate the phantom under a force supplied by the rotation shaft.

19. The system of claim 17, wherein the shield comprises a first shield comprising a first groove, wherein the first groove extends along the first direction, and the screw shaft is disposed inside the first groove.

20. The system of claim 19, wherein the shield further comprises a second shield, a surface of the second field facing the phantom comprising a second groove configured to provide a moving passage for the phantom, wherein the second groove extends in the first direction.

* * * * *